(12) United States Patent
Friedman et al.

(10) Patent No.: US 8,715,679 B2
(45) Date of Patent: May 6, 2014

(54) **PILI FROM *MYCOBACTERIUM TUBERCULOSIS***

(75) Inventors: Richard L. Friedman, Tucson, AZ (US); Jorge A. Giron, Tucson, AZ (US); Christopher J. Alteri, Franklin, MI (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 1538 days.

(21) Appl. No.: 10/588,845

(22) PCT Filed: Feb. 9, 2005

(86) PCT No.: PCT/US2005/003869
§ 371 (c)(1),
(2), (4) Date: Dec. 20, 2006

(87) PCT Pub. No.: WO2005/077003
PCT Pub. Date: Aug. 25, 2005

(65) Prior Publication Data
US 2008/0138356 A1    Jun. 12, 2008

Related U.S. Application Data

(60) Provisional application No. 60/543,109, filed on Feb. 9, 2004, provisional application No. 60/548,899, filed on Mar. 1, 2004.

(51) Int. Cl.
*A61K 39/00*    (2006.01)
*A61K 39/02*    (2006.01)
*C07K 14/00*    (2006.01)
*G01N 33/53*    (2006.01)

(52) U.S. Cl.
USPC ....... 424/185.1; 424/190.1; 435/7.1; 530/350

(58) Field of Classification Search
None
See application file for complete search history.

(56) References Cited

FOREIGN PATENT DOCUMENTS

WO        97 09429        3/1997

*Primary Examiner* — Albert Navarro
(74) *Attorney, Agent, or Firm* — Oblon, Spivak, McClelland, Maier & Neustadt, L.L.P.

(57) ABSTRACT

The present invention relates to pili obtained from *Mycobacterium tuberculosis*, methods of producing the pili and the use of the pili for inducing an immune response against *Mycobacterium tuberculosis*. The present invention also provides proteins and peptides which are constituents of the pili. Antibodies which bind to the pili are also provided.

13 Claims, 9 Drawing Sheets

μg Extracellular Matrix Proteins Proteins

Figure 8

MLARSLSYRHRMYRFACRTLMLAACILATGVAGLGVGAQSAAQTAPVPDYYWCPGQP
FDPAWGPNWDPYTCHDDFHRDSDGPDHSRDYPGPILEGPVLDD**PGAAPPPPAAGGG
A**-COOH

PILI FROM *MYCOBACTERIUM TUBERCULOSIS*

CONTINUING APPLICATION DATA

This application claims benefit to U.S. provisional application Ser. Nos. 60/543,109, filed Feb. 9, 2004, and 60/548,899, filed Mar. 1, 2004, both of which are incorporated herein by reference.

BACKGROUND OF THE INVENTION

1. Field of the Invention

The present invention relates to pili obtained from *Mycobacterium tuberculosis*, methods of producing the pili and the use of the pili for inducing an immune response against *Mycobacterium tuberculosis*. The present invention also provides proteins and peptides which are constituents of the pili. Antibodies which bind to the pili are also provided.

2. Description of the Background

*Mycobacterium tuberculosis* is the bacterial agent responsible for human pulmonary tuberculosis (TB). Almost one third of the world's population suffers from this infectious disease. The *M. tuberculosis* bacillus is highly infectious and is spread by aerosols from infected individuals with active pulmonary disease. Over three million people die yearly from tuberculosis, the largest single infectious cause of mortality worldwide. Tuberculosis is still a persistent health problem in the U.S.A. due in part to the human immunodeficiency virus (AIDS) epidemic. AIDS patients are highly susceptible to infection with *M. tuberculosis* and other non-tuberculosis mycobacteria that seldom infect individuals with intact immune systems. For many bacterial pathogens, the ability to produce proteinaceous adhesins in the form of hair-like structures, called pili, are an important pathogenic attribute since they mediate close interaction and colonization with host cells. Due to the critical role pili play in the establishment of the infectious process and their immunogenecity, pili are considered good candidates for vaccine development.

Although tuberculosis is now recognized as a major public health problem nationally and internationally, there is a need for more information on the basic molecular mechanisms of *M. tuberculosis* pathogenesis and the mechanisms of drug resistance and immunity to this pathogen. Key to tuberculosis pathogenesis is the ability of the bacilli to adhere and enter macrophages and possibly other host cell types, to resist killing, and to replicate in these intracellular sites. The specific molecular mechanisms *M. tuberculosis* uses in these processes are unknown. But the recent DNA sequencing and annotation of the laboratory strain *M. tuberculosis* H37Rv and the clinical isolate CDC1551 genomes have added much to our general knowledge of the genetics of this microbial pathogen.

Adherence to host tissues is an essential and complex first stage for bacterial colonization for the establishment of bacterial infectious disease. In many cases, adherence is mediated by one or more adhesins that can act simultaneously or in distinct steps of an infectious process. Adhesins, in the form of pili or outer membranes proteins, may mediate direct or indirect binding to host cells. Therefore, blocking the interaction of piliated bacteria with host cells through specific anti-pili antibodies represents a feasible strategy for developing an immunoprophylaxis regimen. A great deal of information is available in terms of the interaction and trafficking of *M. tuberculosis* within macrophages of the immune system. It is reasonable to presume that the bacteria are able to express surface molecules devoted to the specific recognition of unique or common receptor components present on target tissues. Nevertheless, the mechanisms underlying the adherence properties of *M. tuberculosis* to the first line of epithelial cells before interacting with professional phagocytes are just beginning to be unraveled. Analysis of the genome sequence of *M. tuberculosis* has revealed various genes coding for putative adhesins and invasins, although their roles in *M. tuberculosis* pathogenesis remain to be determined.

SUMMARY OF THE INVENTION

We have, for the first time, identified and partially characterized pili-like structures on *M. tuberculosis* strains as 2-5-nm-wide fibers that associate into a highly hydrophobic meshwork of variable dimensions. These structures, herein called *M. tuberculosis* pili (or Mtp), are produced in vitro and were demonstrated to react with antibodies present in human convalescent sera obtained from tuberculosis patients. These novel findings have important implications in terms of immunoprophylaxis, prevention and diagnosis of this historically deadly disease.

Thus, the present invention provides isolated and purified pili obtained from *Mycobacterium tuberculosis*.

The present invention also provides a method of producing the pili, comprising subjecting cells of *Mycobacterium tuberculosis* which produce the pili to mechanical shearing, differential centrifugation or isopycnic separation and then isolating the pili from the cells.

The present invention also provides an antibody against pili from *Mycobacterium tuberculosis* for diagnosis and treatment.

In another embodiment, the present invention provides a method of inducing an immune response against *Mycobacterium tuberculosis*, comprising administering an effective amount of *Mycobacterium tuberculosis* pili to a subject.

The present invention also provides a method of detecting a *Mycobacterium tuberculosis* infection in a subject, comprising assaying a body fluid from the subject for the presence of an antibody to *Mycobacterium tuberculosis* pili.

The present invention additionally provides an isolated and purified amino acid sequence which comprises the sequence of SEQ ID NO: 1, 2, 3 or 5.

In another embodiment, the present invention provides a peptide fragment of the amino acid sequence of SEQ ID NO: 2 or 5 which is immunogenic.

The present invention also provides nucleic acid sequences which encode these amino acid sequences.

In another embodiment, the present invention provides a method of producing the amino acid sequences, comprising transforming a host cell with a nucleic acid which encodes the amino acid sequence, wherein the host cells produces the amino acid sequence, and collecting the amino acid sequence.

The present invention also provides an antibody which binds with high affinity and specificity to the amino acid sequences described above.

The present invention also provides methods of inducing an immune response against *Mycobacterium tuberculosis*, comprising administering an effective amount of the amino acid sequences discussed above to a subject.

The present invention also provides a method of detecting a *Mycobacterium tuberculosis* infection in a subject, comprising assaying a body fluid from the subject for the presence of the antibodies discussed above.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 8: Predicted amino acid sequence of *M. tuberculosis* CDC1551 gene MT3413 (SEQ ID NO: 2). Bold sequence indicates the peptide fragment identified by LC-MS/MS as described in the text (SEQ ID NO: 1). Shaded sequence represents the synthesized peptide (SEQ ID NO: 3) used as an immunogen to generate antisera to be utilized in ongoing studies to identify the pili structural subunit.

DETAILED DESCRIPTION OF INVENTION

Figure 1:
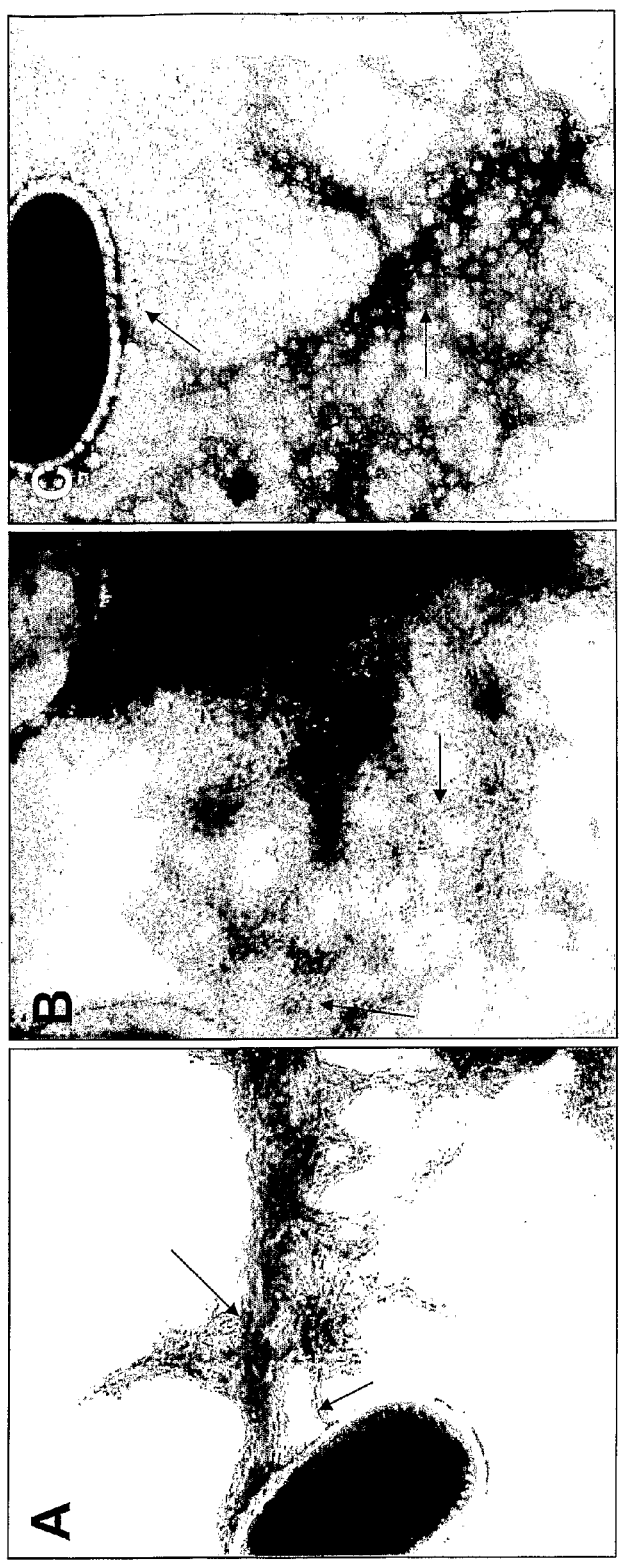
FIGS. 1A, 1B and 1C: *Mycobacterium* species produce pili. Electron micrographs showing different pili morphotypes produced by *M. tuberculosis* H37Ra (A) (×28000); *M. tuberculosis* H37Rv (B) (×25000); *M. tuberculosis* CDC1551 (C) (×22000); Arrows point to the fibers produced by the various strains tested.

Production of pili by *M. tuberculosis* may be of critical importance for the pathogen to interact with target sites on the surface of epithelial cells and macrophages to favor establishment of the pulmonary disease. Several important considerations arise from our data: i) that *M. tuberculosis* does produce pili which could contribute to the virulence properties of these bacteria; ii) antibodies in TB patient sera recognize Mtp demonstrating they are produced during human infections; and iii) antibodies against Mtp might be used to prevent TB infection.

*Mycobacterium tuberculosis* is an important worldwide cause of pulmonary disease in humans. We have discovered a potential adherence factor called *M. tuberculosis* pili, or Mtp, which may permit colonization and adherence of this microorganism to human eukaryotic cells in the lungs. Most importantly, 60% of the convalescent TB patient sera tested reacted with the purified pili, by both immunofluorescence and ELISA. This suggests that the pili are produced in vivo during natural infections and stimulate a humoral immune response. Because of these properties, this factor can be used in the development of a new vaccine to prevent tuberculosis in humans or in a serological diagnostic test.

Bacterial structures called pili play a role in adherence of microorganisms to mammalian epithelial cells in a variety of diseases. Pili and other bacterial adherence factors have been successfully used in the development of effective vaccines against various infectious diseases. No pili have, until now, been identified in *M. tuberculosis*. Thus our discovery is new and novel because it is the first time that a pili-like adhesin has been identified in the human pathogen *M. tuberculosis*. A vaccine developed using purified Mtp could potentially induce antibody production that would block adherence of the bacilli to respiratory epithelial cells in humans and thus prevent initial colonization and infection. Thus, *M. tuberculosis* pili have great potential for use in the development of a new and possibly more effective vaccine against this highly deadly human disease. In the U.S. and all over the world there is a critical need for the development of more effective vaccines against tuberculosis. Major research groups in industry and at major academic institutions are actively pursuing research and development of new anti-tuberculosis vaccines. Additionally, *M. tuberculosis* pili may potentially be used in the development of new methods to diagnose cases of human tuberculosis.

Data presented below show that *M. tuberculosis* is able to produce surface appendages resembling pili. The criteria for calling these structures pili are: 1) their morphology and dimensions are similar to those of the pili of other bacteria, 2) using standard methods to isolate pili from other microorganisms, we have been successful in purifying these pili structures from *M. tuberculosis* and 3) Mtp binds to extracellular matrix proteins (ECM). These observations may open a new avenue to further understand the pathogenic mechanisms of this deadly human pathogen.

One aspect to the present invention is the isolated and purified pili obtained from *Mycobacterium tuberculosis*. The term isolated and purified in this context means that the pili are substantially separated from the cells of *Mycobacterium tuberculosis* as described herein. Thus, the purified pili are substantially free of cells of *Mycobacterium tuberculosis*.

Purity may be judged by visualization of the fibers and absence of cells or other membrane and cell "debris" by transmission electron microscopy (TEM) and negative staining. Additionally the purity is measured by SDS-PAGE (sodium dodecyl sulfate polyacrylamide gel electrophoresis). Preferred preparations lack any major contaminating proteins by SDS-PAGE and have been enriched to have copius amounts of Mtp fibers by TEM.

Such a composition may have a purity such that at least >99% of the non-pili cellular material from *Mycobacterium tuberculosis* has been removed, preferably at least 90%, 95%, 98% or more of the non-pili protein and other material from *Mycobacterium tuberculosis* has been removed. In one embodiment both the BCA protein assay (Pierce) and absorbance at 260/280/320 nm indicates the Mtp preparation prepared according to the present invention contains 14 mg total protein from 100 agar plates containing confluent *M. tuberculosis* growth.

The pili are composed of a dense network of individual fibers which have a tendency to aggregate. The diameter, i.e., thickness, of the fibers generally ranges from about 2 to about 7 nm and when the diameter of a large number of fibers are measured, the average diameters is about 5 nm. The length of the fibers is generally at least about 5 to about 10 microns. The length of the fibers can be difficult to measure since they have a natural tendency to curl. When measured from the surface of cells of *Mycobacterium tuberculosis*, the meshwork of fibers extends from about 5 microns to about 10 microns. The pili display remarkable stability in a range of pH, temperature, detergents, and denaturants, likely due to their extreme hydrophobicity and insolubility.

The pili may be isolated from cells of *Mycobacterium tuberculosis* by subjecting cells of *Mycobacterium tuberculosis* which produce the pili to mechanical shearing, differential centrifugation or isopycnic separation and then isolating the pili from the cells. Such a procedure is described in additional detail below.

The present invention also provides an antibody having specificity for pili from *Mycobacterium tuberculosis*. This is an antibody which is capable of binding to Mtp under normal physiological conditions and which can be used for diagnosis or treatment of TB. Generally, antibodies are proteins that have a natural "high-affinity" for some specific sequence of amino acids of a protein antigen. Affinity is defined as the measure of a single antibody-antigen interaction. When using antibodies in experiments or assays, the conditions are controlled to promote the highest binding while maintaining their specificity e.g., eliminating non-specific binding or background.

Generally, the conditions at which the highest affinity is observed will be normal physiological conditions 37° C., pH 7.4 (neutral) and usually in the presence of a pH buffer to maintain neutral pH such as PBS (phosphate buffered saline) which has 10 mM phosphate, 150 mM NaCl, pH 7.4.

The present invention also provides a method of inducing an immune response against *Mycobacterium tuberculosis*, comprising administration of an effective amount of *Mycobacterium tuberculosis* pili to a subject. Methods of administering a substance to induce an immune response are well-known in the art. In a preferred embodiment, the pili are isolated and purified, for example, as described above. In another embodiment, the subject is a human. Routes for using Mtp as an immunogen to protect humans from TB infection would include but are not limited to, intravenous injection of Mtp and appropriate adjuvant, intranasal inoculation with Mtp, intramuscular injection with Mtp, or inoculation with DNA vaccine comprised of the vaccine vector containing Mtp gene sequence. In another embodiment, Mtp would be administered intradermally.

The present invention also provides a method of inducing an immune response against *Mycobacterium tuberculosis*, comprising administering of an effective amount of nucleic acid encoding a *Mycobacterium tuberculosis* pilin protein to the subject. Thus, the present invention provides a nucleic acid vaccine. A representative nucleic acid is SEQ ID NO: 4) shown below:

```
atgtaccggttcgcgtgccgcacgctcatgctggcggcgtgcatcctgg
ccacgggtgtggcgggtctcggggtcggcgcgcagtccgcagcccaaac
cgcgccggtgcccgactactactggtgcccggggcagcctttcgacccc
gcatggggggcccaactgggatccctacacctgccatgacgacttccacc
gcgacagcgacggccccgaccacagccgcgactacccccggacccatcct
cgaaggtcccgtgcttgacgatcccggtgctgcgccgccgcccccggct
gccggtggcggcgcatag
```

The nucleic acid may also encode an immunogenic fragment of a pilin protein, such as those described above. Accordingly, a suitable fragment of SEQ ID NO: 4 may be used. The present invention also includes isolated and purified nucleic acids which The present invention provides a method by which monoclonal pili antibodies are derived using mice and standard hybridoma techniques The present invention provides a method by which polyclonal pili antibodies are derived using rabbits.

The present invention also provides a method of detecting a *Mycobacterium tuberculosis* infection in a subject, comprising assaying a body fluid from the subject for the presence of an antibody to *Mycobacterium tuberculosis* pili. In a preferred embodiment, the subject is a human and the body fluid is serum. The general protocol for antibody detection assays are ELISA and dot-blot or their many derivations. In other embodiments respiratory aspirates or lavage and saliva are the body fluid tested.

The present application also provides the amino acid sequence SEQ ID NO: 2, which is shown in FIG. 8, and SEQ ID NO: 5. SEQ ID NO: 1 and 3 are subfragments of SEQ ID NO: 2 and 5, as discussed below. Thus, the present invention provides an isolated and purified amino acid sequence which comprises SEQ ID NO: 1, 2, 3 or 5. Those sequences are listed below:

```
                                           SEQ ID NO: 1
PGAAPPPPAAGGGA

SEQ ID NO: 2
MLARSLSYRHRMYRFACRTLMLAACILATGVAGLGVGAQSAAQTAPVPDY

YWCPGQPFDPAWGPNWDPYTCHDDFHRDSDGPDHSRDYPGPILEGPVLDD

PGAAPPPPAAGGGA

SEQ ID NO: 3
CHDDFHRDSDGPDHSRDYPG

SEQ ID NO: 5
MYRFACRTLMLAACILATGVAGLGVGAQSAAQTAPVPDYYWCPGQPFDPA

WGPNWDPYTCHDDFHRDSDGPDHSRDYPGPILEGPVLDDPGAAPPPPAAG

GGA
```

The present invention also provides an amino acid sequence which is a peptide fragment of the amino acid sequence of SEQ ID NO: 2 or 5 which is immunogenic. The term "peptide fragment" refers to a portion of SEQ ID NO: 2 or 5, i.e., at least one N- or C-terminal amino acid residue is deleted.

The present invention also provides isolated and purified nucleic acids which encode the amino acid sequences. Since the amino acid sequences are known and the genetic code is known, one can readily envision any such sequence.

The present invention also provides a method of producing the amino acid sequences by transforming a host cell with a nucleic acid which encodes the amino acid sequence, wherein the host cells produces the amino acid sequence, and collecting the amino acid sequence. Bacterial cells are suitable host cells. *E. coli* are especially preferred. Alternative hosts are *Streptomyces* or yeast expression technology.

The present invention also includes antibodies which bind to the amino acid sequences with high affinity to the amino acid sequences described above. The discussion of antibodies above applies to this embodiment of the invention as well.

The present invention also provides methods of inducing an immune response against *Mycobacterium tuberculosis*, comprising administering an effective amount of the amino acid sequences discussed above to a subject. The present invention also provides a method of detecting a *Mycobacterium tuberculosis* infection in a subject, comprising assaying a body fluid from the subject for the presence of the antibodies discussed above. Humans are the preferred subjects and serum is a preferred body fluid.

1. *Mycobacterium Tuberculosis* Produces Pili Structures.

In the course of ultrastructural studies of pathogenic and attenuated strains of *M. tuberculosis* by negative staining and transmission electron microscopy (TEM), we noted the presence of fibrillar structures resembling pili (also called fimbriae) when the bacteria were propagated under suitable laboratory growth conditions. Namely, cultures of various *M. tuberculosis* strains (avirulent H37Ra, virulent H37Rv and CDC1551) were grown on 7H11 agar plates containing OADC for three weeks at 37° C. Plate grown bacteria were gently suspended in 4% formaldehyde and incubated overnight in a microfuge tube. The bacteria were negatively stained with 1% phosphotungstic acid (pH 7.4) on Formvar-coated copper grids and then observed in a Phillips CM12 electron microscope at 80 kV. All of the *M. tuberculosis* structures observed were bacterial in nature and not artifacts present in the bacterial growth media employed. We prepared electron microscopy grids with liquid medium or with water sitting on solid agar medium that had been incubated for the same time as inoculated cultures. In these control studies we did not observe any fibrillar structures, indicating that the fibers seen in *M. tuberculosis* cultures were of bacterial origin.

We were then interested in studying the effect of culture conditions on the production of pili by H37Ra, H37Rv, and CDC1551. To this aim, we used a panel of liquid and solid media (Table 1) for bacterial growth and qualitatively determined the level of pili production by negative staining and TEM. *M. tuberculosis* strains were plated as a lawn and grown for a period of 3 weeks at 37° C. in a 5% $CO_2$ atmosphere. *M. tuberculosis* broth cultures in 7H9 were grown for 2 to 3 weeks and GAS broth cultures were grown for 5 weeks until both reached an $OD_{650}$ of 1.50. The data summarized in Table 1 indicates that Mtp are likely controlled by environmental stimuli since the level of pili production varied depending on the growth media used. Further, the qualitative analysis demonstrates that the avirulent strain of *M. tuberculosis*, H37Ra, has a diminished capacity to produce pili as compared to H37Rv and CDC1551. Strikingly, the greatest difference between virulent and attenuated *M. tuberculosis* was observed in broth grown cultures, where *M. tuberculosis* H37Ra produces nearly undetectable levels of pili, while *M. tuberculosis* H37Rv and CDC1551, the clinical isolate, produce the highest level of pili in the culture conditions tested. Ten to 25% of *M. tuberculosis* H37Rv and CDC1551 grown in either 7H9 or GAS broth contained pili as observed by TEM.

In conclusion, we have for the first time shown that *M. tuberculosis* produces pili structures and their production is under the control of environmental growth conditions.

TABLE 1

*M. tuberculosis* pili production on various media as observed by TEM[1]

| Strain | 7H11 agar + OADC | 3% Sheep Blood Agar | 7H10 agar + glycerol | 7H11 agar + glycerol | 7H10 agar + glucose | RPMMA Agar*** | 7H9 broth + OADC + Tw* | GAS** broth + Tw* |
|---|---|---|---|---|---|---|---|---|
| H37Ra | + | ++ | + | ++ | + | – | – | – |
| H37Rv | + | ++ | + | + | + | – | +++ | +++ |
| CDC1551 | + | ++ | +[2] | +[2] | +[2] | + | +++ | ++ |

[1]All plate grown cultures in the table were incubated in a 5% $CO_2$ atmosphere;
[2]Very limited growth was observed in these conditions;
*Tween 80 (Tw);
**glycerol-alanine salts (GAS) medium (58).),
***RPMMA (reduced phosphate modified minimal A) agar is a defined minimal media on which mycobacteria can be grown (personal communication, James Megehee).
+++ 10 to 25% of *M. tuberculosis* contain pili,
++ 5 to 10% bacteria contain pili,
+ less than 5% bacteria contain pili,
– undetectable levels of pili.

strains analyzed produced thin (2-5 nm-wide), aggregative, flexible hair-like appendages that protruded several microns away from the bacterial cell surface (FIGS. 1A, B and C). The fine fibrillar structures, herein called *M. tuberculosis* pili or Mtp, tended to aggregate to each other forming a meshwork of variable dimensions that appeared associated with the bacteria or free in the supernatants. As a particular note, these fibrillar structures are morphologically reminiscent of the well-characterized curli structures produced by some enteric bacterial pathogens. Under these growth conditions, 5% of the bacterial cells present in the culture samples analyzed by TEM possessed pili. Studies were done to confirm that the pili 2. Identification and Purification of *M. Tuberculosis* Pili (Mtp).

Figure 2:
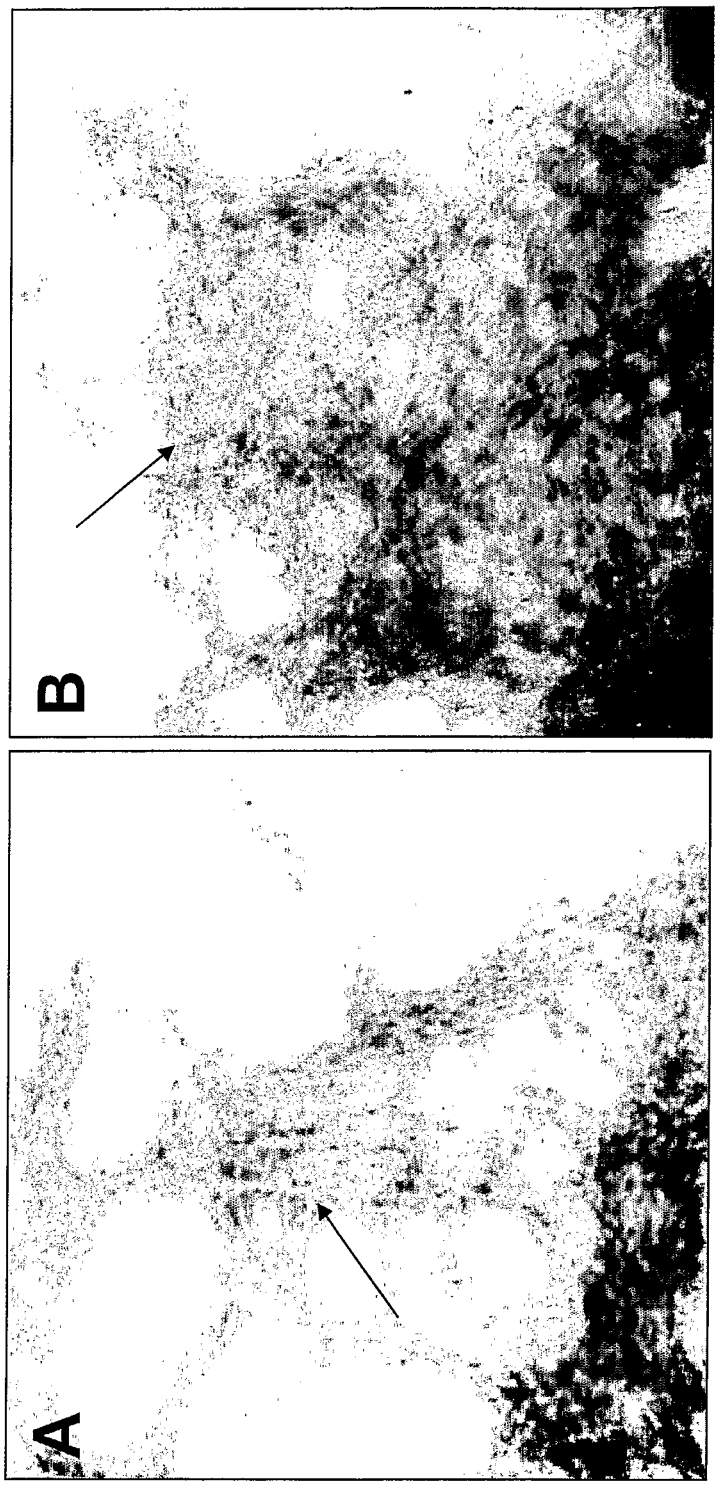
FIGS. 2A and 2B: Electron micrographs of *M. tuberculosis* pili (Mtp) enriched extracts. A and B, Purified pili from *M. tuberculosis* H37Ra (×25000).

Our next goal was to purify and identify the nature of the pili structures observed in *M. tuberculosis* cultures. For safety reasons and ease of working under non-BSL-3 conditions, *M. tuberculosis* H37Ra was used for pili purification. H37Ra was grown at 37° C. under a 5% $CO_2$ atmosphere for three weeks on one hundred 7H11 agar plates supplemented with OADC (Table 1). Cultures were Gram stained and acid-fast stained to confirm purity of the bacterial preparations. The heavy bacterial lawn obtained was harvested from the plates into 150 mM mono-ethanolamine buffer (pH 10.5) and the pili were mechanically sheared from the surface of the bacteria. The bacteria were separated by repeated low speed centrifugation and the supernatant containing pili was extracted with 2:1 choloroform:methanol to remove vesicular material. The upper aqueous phase and interphase that contained pili fibers was recovered. This fraction was centrifuged at 18,000×g to completely remove bacteria, bacterial membranes and debris. The supernatant fraction containing the pili was then recovered and concentrated by ultracentrifugation for several hours at 4° C. The pelleted pili was resuspended in PBS and dialyzed to remove any salts. This preparation was further analyzed by TEM, which revealed the presence of abundant pili aggregates (FIG. 2A) morphologically identical to those observed associated with the bacteria (FIG. 1A). The approximate yield of Mtp from one hundred 7H11 agar plates was 14 mg of total protein, as determined by absorbance at $OD_{280}$ as compared to a bovine serum albumin (BSA) standard curve. A representative, non-limiting example of a procedure to purify M. tuberculosis pili is provided below:

1. Dilute 1 ml frozen stock of M. tuberculosis cells in 10 ml 7H9+ADC containing 0.05% TWEEN-80 and incubate at 37° with shaking for 48-72 h to prepare starter culture.
2. Inoculate 100 Middlebrook 7H11+glycerol agar plates with 100 μL starter culture of *M. tuberculosis* and incubate at 37° until a heavy lawn of growth is observed, 10-14 days. Remove loopful of growth to 1 ml $dH_2O$ gently vortex to resuspend and prepare sample for TEM to verify production of pili fibers.
3. Harvest *M. tuberculosis* from the plates, using a glass spreader, 15 plates into a beaker containing 60 ml 150 mM ethanolamine buffer pH 10.5. Portion the suspension into two 50 mL conical tubes and add 3 mm glass beads to each tube. Repeat the procedure for the remaining plates, for 100 plates use approximately 250 ml ethanolamine buffer and 8 conical tubes. Vortex the tubes full power for 1 min, followed by vigorous shaking for 3-5 min and allow the tube contents to settle for 1-2 min. Collect the upper 25-30 ml cell suspension and transfer to new tubes.
4. Centrifuge the suspension at 3000 rpm for 60 min to pellet the cells. Recover the supernatant fraction (3KS). Check both 3KS fraction and pellet fraction (3 KP) by TEM to verify presence of pili in 3KS. If necessary resuspend 3 KP in ethanolamine buffer, gently resuspend and centrifuge as described to recover pili that may have been sedimented with the cells. To limit loss of pili into the bacterial pellet, due to clumping of the cells, centrifugation speed was reduced and run time was increased. Repeat 3000 rpm spins for 30 min 2 more times.
5. (Optional) If large amounts of vesicular material is visible in 3KS by TEM, extract the final 3KS fraction with an equal volume of 2:1 chloroform:methanol by vigorously shaking for 5 min. Spin the suspension at 12000 rpm for 10 min to separate the phases. Recover the upper aqueous phase and the interphase that contains the pili fibers.
6. Load the pili fraction in thin-wall polyallomar tubes with anodized aluminum cap assemblies and concentrate fibers by ultracentrifugation at 120,000×g for 3 hr at 4° C. in a fixed angle rotor. Collect the supernatant as fraction 50KS and resuspend the pellet in sterile water as fraction 50 KP. Observe both fractions by TEM. The 50 KP fraction contains rich amounts of aggregated fibers while the supernatant fraction 50KS should be devoid of pili fibers. The approximate yield of protein (pili) from 100 plates by A280 is approximately 14 mg.

3. Initial Biochemical Characterization of Mycobacterial Pili.

Generally, pilin monomers are proteins in the range of 14-25 kDa that can be identified in SDS-PAGE gels after dissociation of the pili filaments under conventional denaturing (in the presence of SDS, 2-mercaptoethanol, and boiling at 100° C.) conditions. However, some bacterial pili types require special chemical treatments such as acidification (pH 1.5) and boiling with HCl, as in the case of the common *E. coli* type I pili, or denaturation with formic acid, as in the case of the *Salmonella* and *E. coli* curli fibers. We began our characterization of purified Mtp preparations in 16% SDS-polyacrylamide gels under normal denaturation conditions. After repeated efforts employing Coomasie Blue and silver staining techniques, we were unable to detect the presence of polypeptide bands in the pili samples in the range of 14 to 25 kDa that correlated with the presence of abundant pili in samples as demonstrated by TEM. The absence of other high MW polypeptide bands and TEM analysis indicated that our pili preparations were relatively pure. This suggested that Mtp were highly hydrophobic and non-dissociable under regular 2-mercaptoethanol and SDS-PAGE denaturation. In fact, we observed the presence of protein aggregates in the wells of the stacking gel confirming that the pili filaments were still intact and therefore the pilins were not entering the gel. Nevertheless, the pili fractions were subjected to N-terminal amino acid sequencing by Edman degradation. Mtp were blocked in their N-terminus. Further efforts employed several different chemical, physical and enzymatic treatments to allow dissociation of the pili aggregates followed by denaturation of the pilin proteins by SDS-PAGE. Isolated Mtp were treated with various chemical reagents that have been used by other groups to resolve pili into their pilin monomers. Formic acid treatment was used in the manner described by Collinson et al. Approximately 0.10 mg of the pili preparation was dried using speed-vacuum centrifugation, resuspended in 95% formic acid, and immediately frozen at −70° C. After 1 h, the sample was dried by heating for 96 h to remove all traces of acid. Pili were also incubated in the presence of 0.1% to 10% SDS at 37° C. for 18 h. Attempts were also made to dissolve the fibers in 2 to 8 M urea or saturated guanidine-HCl for 18 h at 37° C. The purified pili preparations were also incubated in 0.1, 1, and 10% TRITON-X-100 at 37° C. for 18 h. The purified pili were subjected to acid (pH 1.8) or alkaline (pH 12.0) treatments and boiled for 30 min as previously described. The pili fibers were also treated with 0.5%, 1%, and 5% sodium deoxycholate and incubated at 37° C. for 18 h. After the above treatments samples were either prepared for separation by SDS-PAGE or for viewing by TEM. After electrophoresis of all above treated Mtp pili samples, material was still observed in the wells of the stacking gel and no visible protein bands were detected in the separating gel following either Coomasie Blue or silver staining methods. Similar results were observed when a 10% resolving gel was also used. After all of the above chemical treatments pili fibers were still visible by TEM. These results demonstrate that *M. tuberculosis* pili are very stable and cannot be broken down into their pilin subunits by methods conventionally utilized by other research groups working with pili. Further, the purified pili from *M. tuberculosis* were treated with a variety of enzymes to determine their biochemical nature. Pepsin, trypsin, or proteinase K treatment under the appropriate enzymatic conditions and concentrations, as observed by SDS-PAGE analysis and TEM, did not degrade the pili. Due to the aggregative nature of the pili, amino acid residues of the macromolecule may not be accessible for cleavage by these proteases. Treatment of Mtp with the enzyme cellulase had no effect, demonstrating that the pili are not composed of cellulose polymers. The pili were also incubated at 37° C. for 18 h with lysozyme (10 mg/ml) without effect, indicating the fibers are not polymers of peptidoglycan. The purified pili were extracted with 2:1 chloroform:methanol and found to remain in the interface after centrifugation. This indicates that the pili are not a non-polar lipid substance from the mycobacterial cell wall.

Due to the difficulty encountered using traditional biochemical techniques to resolve the composition of the purified Mtp pili fibers a more direct approach was employed involving a combination of enzymatic and chemical manipulations followed by analysis using liquid chromatography and tandem mass spectroscopy (LC-MS/MS). Our earliest attempts at dissociation of the fibers into the pilin subunits suggested that the pili resisted the various biochemical/chemical treatments. Also, due to the large molecular mass of intact fibers, the purified pili were unable to enter gel matrices during electrophoretic separation. Instead, we analyzed the purified pili from M. tuberculosis directly in solution.

Pili isolated from three different M. tuberculosis strains [H37Rv, CDC 1551, and H37Ra] were examined in an effort to identify a common component present in all three pili preparations. Dilute acid hydrolysis normally hydrolyzes peptide bonds at either side of Asp and Asn to generate fragments. A small amount of purified Mtp material was placed in a sealable tube to which 1.1 μl of concentrated HCl (constant boiling quality) was added with 500 μl water. The tube was degassed and nitrogen was added to protect the sample from oxidation. The sealed tube was subjected to boiling at 108° C. for 4 h, material reconstituted in 10-100 μl water, and the samples analyzed by LC-MS/MS using a QTOF2 instrument (Waters, Milford). Masslynx 4.0 was used to generate pkl files from mass spectral data. These pkl files were submitted to inhouse MASCOT searches allowing for 0.8 Da peptide mass tolerance and 0.2 Da fragment mass tolerance.

Upon examination of the LC-MS/MS results, it was found that all three samples analyzed had one common peptide fragment having a monoisotopic mass (Mr) of 1086.55 Da and a sequence of PGAAPPPPAAGGGA (SEQ ID NO: 1) (aa101-114) (FIG. 7A). Mascot uses a probability based score and in all cases, the identification of the fragment 101-114 was considered statistically significant, indicating a true identification. Furthermore, two of the samples produced only this peptide following acid hydrolysis indicating the relative purity of the analytes. Obtaining identical results using three different digested Mtp samples strongly suggests that the identified fragment (FIG. 7) represents a portion of the Mtp structural subunit, the MtpA pilin.

Database BLAST searches indicated that the identified peptide sequence (FIG. 7B) matches the predicted protein encoded by *M. tuberculosis* strain H37Rv ORF Rv3312A and strain CDC1551 gene MT3413 (FIG. 8). The sequence from the H37Rv strain has the following amino acid sequence (SEQ ID NO: 5):

```
MYRFACRTLMLAACILATGVAGLGVGAQSAAQTAPVPDYYWCPGQPFDPA
WGPNWDPYTCHDDFHRDSDGPDHSRDYPGPILEGPVLDDPGAAPPPPAAG
GGA.
```

Additionally, the identified sequence is also found in *M. bovis* ssp. bovis AF2212/97 as gene Mb3314c. The available genome databases of other mycobacterial strains were also examined to determine the conservation of the putative mtpA gene across mycobacterial species. The pilin gene (H37Rv strain) (SEQ ID NO: 4):

```
atgtaccggttcgcgtgccgcacgctcatgctggcggcgtgcatcctggc
cacgggtgtggcgggtctcggggtcggcgcgcagtccgcagcccaaaccg
cgccggtgcccgactactactggtgcccggggcagcctttcgaccccgca
tgggggcccaactgggatccctacacctgccatgacgacttccaccgcga
cagcgacggccccgaccacagccgcgactaccccggacccatcctcgaag
gtcccgtgcttgacgatcccggtgctgcgccgccgcccccggctgccggt
ggcggcgcatag
``` was found to be absent in the other mycobacterial genomes, indicating that the gene is restricted to members of the *M. tuberculosis* complex. Outside of the indicated mycobacterial strains, the putative mtpA gene does not have any similarity to any prokaryotic or eukaryotic sequences deposited in the databases at NCBI. The putative mtpA gene is one of three conserved hyothetical proteins surrounded by intermediary metabolic genes (FIG. 9). Because most pili characterized belong to Gram-negative bacteria it is not surprising that the genomic organization of mtpA in *M. tuberculosis* H37Rv does not resemble known pili biogenesis operons.

4. Detection of Antibody to *M. Tuberculosis* Pili in Sera from Tuberculosis Patients.

An initial study was done to determine if anti-pilus antibody is present in sera from human patients with active tuberculosis infections. If such antibody could be detected, it would suggest that *M. tuberculosis* pili are produced in vivo during natural human infections and that they are antigenic. Toward this aim, sera from thirty-six cavitary tuberculosis patients, admitted to the Instituto Mexicano del Seguro Social, Monterrey, Mexico and sera from five healthy controls were obtained. The sera were tested against purified Mtp preparations obtained from H37Ra using immunofluorescence (IF) as previously described. Briefly, glass cover slips were prepared with a diluted pili preparation, air-dried, and fixed with PBS containing 3% formaldehyde overnight at 4° C. The coverslips were washed with PBS followed by incubation at room temperature for 1 h in sera diluted 1:1,000 in PBS containing 10% fetal calf serum (PBS/FCS). After thorough washing with PBS, to remove unbound antibody, the samples were incubated for 1 h with goat anti-human IgG Alexa Fluor 488 (Molecular Probes) diluted 1:5,000 in PBS/FCS. The coverslips were washed and mounted on glass slides before observation under a Nikon TE 2000S fluorescent microscope using Metacam software. Strikingly, we found that a high percentage (60%) of the sera from tuberculosis patients reacted very strongly with the purified pili preparation (FIGS. 3A, B, C, and D). We considered the reaction positive when long fluorescent coiled fibers were observed after incubation with the patients' sera. No fluorescent filaments were observed with the goat anti-human IgG ALEXA FLUOR 488 alone, confirming the specificity of the reaction (data not shown). More interestingly, 5 of 5 sera from healthy human controls did not react with Mtp fibers (FIG. 3E).

Further evidence that TB patient sera contain antibodies that recognize Mtp fibers was obtained by ELISA assays. Microtiter plates were coated with purified Mtp fibers, incubated with serial dilutions of TB patient sera, followed by incubation with anti-human IgG HRP conjugate. The ELISA analyses indicated that 60% (n=36) had IgG titers greater than 3,200 while healthy control sera (n=5) did not react significantly with Mtp (FIG. 4). Nearly all the individual TB patient sera that reacted strongly with purified Mtp by IF, had anti-Mtp IgG titers higher than 3,200. Taken together these data demonstrate that Mtp are produced by *M. tuberculosis* during natural human TB infections, indicating that they are expressed in vivo. The studies also show importantly that Mtp are antigenic, and the host immune response to Mtp may correlate with disease.

5. Adherence of Mtp to Extracellular Matrix Proteins.

Extracellular matrix proteins (ECM) such as fibronectin, collagen, laminin, and vitronectin act as interlinking molecules in connective tissues and are ideal microbial adhesion targets for colonization of host tissues. Studies were done to determine if Mtp has affinity for ECM. For these experiments a sandwich based ELISA assay was employed using 1.5 μg of Mtp immobilized onto ELISA microtiter plate wells and blocked with PBS Superblock (Pierce) prior to the addition of increasing concentrations of fibronectin, laminin, and collagen IV (Sigma). After incubation and wash steps the bound ECM proteins were detected using either a 1:5000 dilution of rabbit anti-fibronectin, anti-laminin, or mouse monoclonal anti-collagen IV antibodies (Sigma). The anti-ECM antibodies were detected using a 1:5000 dilution of anti-rabbit or anti-mouse peroxidase conjugates (Sigma) and this complex was detected using a TMB single solution substrate (Zymed). The reaction was stopped with 1N HCl, and absorbance was read at 450 nm using a microtiter plate reader. The results indicate that purified Mtp fibers bind laminin and fibronectin in a dose-dependent manner, and do not significantly bind to collagen IV (FIG. 5). Clearly Mtp has a strong affinity for binding to laminin and to a lesser extent fibronectin.

The binding of the pili to laminin strongly implicates Mtp as an adhesin for *M. tuberculosis*. These results provides evidence for the role of Mtp in human disease as ECM proteins are important elements in the epithelial substrata of the lung and other organ systems which can be exposed during tissue damage due to an inflammatory response to a TB infection. Thus, Mtp may play a role in *M. tuberculosis* adherence and colonization in the lung during infection.

6. Ultrastructural Analysis of Biofilm-Like Communities and Demonstration of Fibrillar Structures.

Many environmental and pathogenic bacteria live in communities tightly associated to biotic and abiotic surfaces. These so-called biofilms are intrinsic ways in which the bacterial pathogens protect themselves from the bactericidal activity of antimicrobial drugs or from the clearance mechanisms of the body. There are virtually no reports on the capacity of *M. tuberculosis* to form biofilms. Plate-grown *M. tuberculosis* H37Ra was washed in HBSS and seeded at $10^7$ bacteria/ml onto glass cover slips in RPMI. We captured the bacilli attaching to the glass substratum after incubation for 3 h at 37° C. in a 5% $CO_2$ atmosphere, followed by fixation with 3% formalin, and processing for scanning electron microscopy (FIG. 6). The bacilli appeared to produce a massive meshwork of fibrous matter (resembling pili) that tethers the bacteria, which we presume, allows the formation of biofilm-like communities. Pili, such as type IV and curli, have been implicated in biofilm formation.

EXAMPLES

General Methods

Human Monocytes.

Human monocytes will be isolated from heparinized venous blood by Ficoll-Hypaque gradient centrifugation (27) and further purified using fibronectin adherence on gelatin coated flasks (133). Adherent monocytes will be recovered and added to 24-well tissue culture plates at a concentration of $2\times10^5$ monocytes/well in 1640 media containing 10% autologous human serum. Monocytes will be incubated at 37° C. in a $CO_2$ incubator for 2 to 7 days before use in various assays. Purity of the monocyte preparation will be determined by Wright stain, and viability will be determined by trypan blue exclusion.

Bacteria.

Mycobacterial strains (*M. tuberculosis* H37Rv, *M. tuberculosis* H37Ra, *M. tuberculosis* CDC1551, *M. smegmatis*) and *E. coli* strains (to be used in cloning of *M. tuberculosis* genes) will be stored as stock cultures at −70° C. as thick suspensions in either Middlebrook 7H9 [mycobacteria] or LB [*E. coli*] medium containing 30% glycerol. Mycobacterial inocula for various experiments will be prepared by spreading several drops of a freshly thawed bacterial suspension to Middlebrook 7H10 agar plates which will be incubated at 37° C. [three weeks for *M. tuberculosis*, three days for *M. smegmatis*] (9). Liquid cultures will be grown in Middlebrook 7H9 medium. For growth of *M. tuberculosis* H37Rv, H37Ra, and CDC1551 bacteriological media (plates and liquid) will include 10% oleic acid-albumin-dextrose-catalase supplement (OADC) and 0.05% TWEEN-80 in liquid cultures only (90). The bacilli will be harvested and diluted to appropriate concentrations for use in the various studies, following procedures described above. Purity of cultures will be monitored by both acid-fast and Gram staining and by culturing on blood agar plates.

Statistical Analysis.

The significance of differences between results will be calculated by the analysis of variance (ANOVA). All significant differences between groups identified by two-way ANOVAs at the 95% confidence level or greater will be confirmed by post-hoc testing.

Example 1

Produce Serological Tools for Evaluating Mtp

Background/Rationale.

There are no reports on the presence of pili produced by *M. tuberculosis* or any other mycobacterial species. Several lines of evidence demonstrate that *M. tuberculosis* produces pili structures. Generally, pili are recognized as virulence factors since their presence enhances the ability of bacteria to adhere, colonize, and even invade epithelial cells (100). They are also potential vaccine candidates for inducing protective antibodies to block adherence and colonization (102). Therefore, antibodies against Mtp are critical to the development and evaluation of improved TB diagnosis and treatment strategies.

1. Production of Affinity-Purified Antibody Against Mtp.

To characterize Mtp and its potential function in *M. tuberculosis* pathogenesis, affinity-purified rabbit antibodies against Mtp will be produced. Anti-Mtp antibody will be a useful tool in determining the role of Mtp in the interaction of *M. tuberculosis* with cultured host cells. The ability of anti-Mtp antibody to block bacterial adherence and/or invasion of host cells will be evaluated in inhibition of adherence assays as described in Example 3. Further, anti-Mtp antibody will also be used to monitor Mtp expression in clones and isogenic mutants to be constructed in Example 2. Antisera will be produced for these studies by Quality Controlled Biochemicals (QCB), Inc., Hopkinton, Mass. Antibodies against Mtp (purified as described above) will be raised in New Zealand rabbits by subcutaneous and intramuscular injections of purified Mtp (150 μg/dose) with complete Freund's adjuvant in the first dose and with incomplete Freund's adjuvant in the following doses. Rabbits (two total) will be boosted five times and test bleeds will be taken at each stage to monitor antibody titers against Mtp by ELISA performed as described above. The presence of specific antibodies will also be tested by IF microscopy as described above. Once a means is devised to denature Mtp into its pilin monomers or when a His-tagged- MtpA protein is produced in E. coli (see Example 2, section 2b below), Western blot analysis will also be used to test the antisera. Antibodies generated against Mtp will then be affinity-purified. In brief, rabbit serum will be passed over an agarose-based column prepared with either purified Mtp or Mtp pilin monomers chemically bound to it. The column will be washed with PBS and bound antibodies will be eluted using a low pH glycine buffer before dialysis in PBS. Alternatively, if problems arise with successfully binding Mtp to the agarose resin, then antibody will be purified by batch absorption using purified Mtp. Rabbit serum will be mixed with Mtp for several hours or overnight and Mtp with bound antibody will be recovered by ultracentrifugation, since in our initial studies we observed that Mtp can be isolated by high speed centrifugation. The bound antibodies will then be eluted using low pH buffer as described above. These affinity-purified antibodies will be stored frozen at −70° C. until use.

2. Construction and Production of his-Tagged-MtpA Protein.

Since presently we have been unable to denature native Mtp into its pilin monomers, the mtpA gene (SEQ ID NO: 4) will be subcloned into a His-tagged expression vector system and overexpressed in E. coli. The availability of pilin protein would be useful in many of the proposed studies in this grant application. His-tagged-MtpA will be overexpressed using standard non-proprietory techniques. Host cells will be harvested and disrupted by sonication. Total lysates will be batch absorbed to nickel-NTA agarose under denaturing conditions in a urea buffer. The nickel agarose will be washed, recovered by low speed centrifugation, and poured into a chromatographic column. After further washing, the His-tagged-MtpA protein will be eluted from the column with buffer containing imidazole, according to standard protocols. Eluted His-tagged-MtpA will be dialyzed against PBS to remove urea and imidazole. SDS-PAGE, Western blot analysis, and two-dimensional gel electrophoresis will be used to monitor purification of the MtpA protein. If problems occur using histidine tags, then other affinity tags are available (glutathione-S-transferase [GTS], maltose binding protein, thioredoxin, etc) and will be used.

3. Production of Antibodies Against his-Tagged MtpA Pilin and Mtp-Derived Peptides.

The mtpA gene will be subcloned into a His-tagged expression vector and will be used to overexpress MtpA pilin in E. coli and purified by nickel-agarose chromatography. See Example 2, section 2b for details. Using the deduced amino acid sequence of mtpA we will also be able to select candidate immunogenic regions and potential homologous host cell binding sites of the MtpA molecule for designing peptides. We estimate that five to ten peptides would be designed for this purpose. The immunogenic regions of MtpA will be determined and mapped using the HLA Peptide Binding Prediction software available on the NIH website (http://bimas.dcrt.nih.gov/molbio/hla_bind/) and possible host cell binding sites will be determined. Then Mtp 16-mer peptides to these selected regions will be synthesized to 95% purity. The peptides conjugated to the carrier protein KLH by a cross linker, and His-tagged-MtpA will be used to immunize rabbits, and antisera will then be affinity-purified as described above. These anti-MtpA pilin and anti-MtpA-peptide antibodies will be used in inhibition of adherence experiments in Example 3. Other studies will also be done to determine the important epitopes of Mtp that are required for binding to host cells as well as in determining what regions carry immunogenic epitopes on the MtpA molecule.

Figure 3:
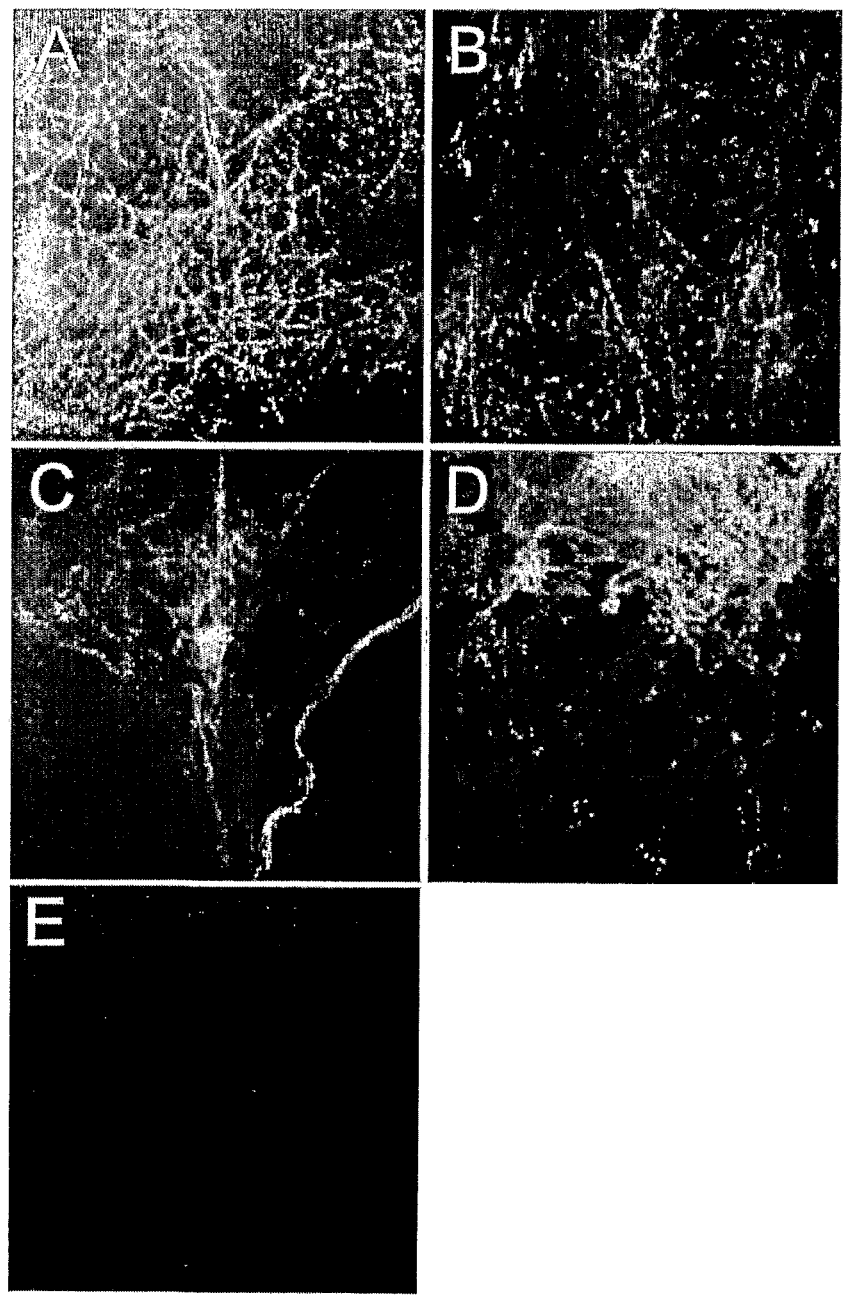
FIGS. 3A, 3B, 3C, 3D and 3E: Reaction of TB patient sera with purified Mtp. Mtp (FIG. 2A) were reacted with human TB patient sera HS14, (A), HS7 (B), HS35 (C), HS29 (D), and healthy control sera (E) and detected with anti-human IgG FITC-conjugate. Positive reactions (A-D) are depicted by the presence of fluorescent fibers. No reactivity was observed with healthy control sera (E). Magnification of fluorescence micrographs A-E ×1000.
Figure 4:
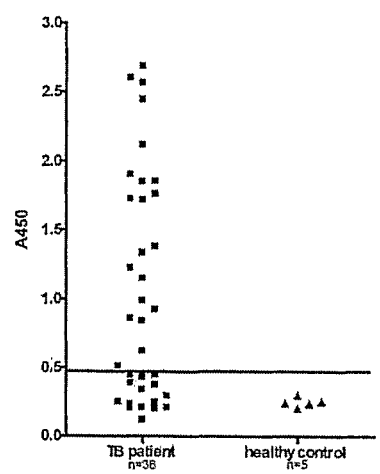
FIG. 4: Sera from TB patients react to purified Mtp. Sera from TB patients (n=36) and from healthy controls (n=5) were tested for the presence of anti-Mtp antibodies by ELISA using immobilized Mtp fibers. Most of the patient sera (60%) showed a significant titer against Mtp fibers. Results presented obtained at sera 1:3200 dilutions run in triplicate. The horizontal line indicates the cut-off value of two times the average ELISA titer $A_{450}$ reading of healthy control sera.

The MtpA pilin monomer and peptides will also be used to determine their immunologic reactivity with sera from tuberculosis patients. These studies will be done using sera from TB patients (a total of 36) that we have already obtained and sera from 20 healthy controls will be collected. ELISA assays will be done with Mtp, pilin, and MtpA peptides to determine which proteins are reactive with the sera (156). In brief, ELISA plates will be coated by drying down the MtpA peptides, Mtp or pilin (1.25 µg/ml) onto wells, washed, and blocked with SuperBlock (Pierce). Antibody titers will be determined via ELISA assays following procedures described above. Levels of total IgG as well as levels of IgG1 and IgG2a isotypes will be measured to determine whether Mtp induce either a Th1 or Th2-type immune response. Induction of a strong IgG2a response is indicative of a Th1-type immune response, while a dominant IgG1 response is usually associated with a Th2-type immune response (129). While we know that 60% of the TB sera are reactive with native Mtp (by IF and ELISA, See FIGS. 3 and 4), it will be interesting to determine if these same sera are reactive with the Mtp pilin monomer or its derived peptides. It is predicted that the patient sera will give positive ELISA results using the Mtp monomer and some of the Mtp peptides. These results will help to determine the key immunogenic epitopes on Mtp that induce a humoral immune response during a human tuberculosis infection. One or more of these peptides may possess protective epitopes.

Example 2

Production of Recombinant Mtp in Non-Tuberculosis *Mycobacteria*

1. Utilization of *Mycobacterium smegmatis* to Produce Mtp.

*M. smegmatis* is an ideal strain to use to express and produced Mtp in the proposed experiments. *M. smegmatis* is closely related to *M. tuberculosis* and has been demonstrated in various investigations to readily express genes from *M. tuberculosis* (144-147) and from other mycobacteria (148-150). Our studies have found that while *M. smegmatis* does produce pili, they are morphologically and antigenically different than Mtp. *M. tuberculosis* H37Rv genomic DNA libraries prepared in the vector pOLYG, as previously described (26), will be used in these experiments. *M. smegmatis* containing the *M. tuberculosis* plasmid libraries will be plated on 7H10 agar plates containing hygromycin B and colonies will be screened for the production of Mtp by colony immunoblotting using specific anti-Mtp antibody that will be pre-absorbed with *M. smegmatis* 1-2c cells to remove any cross-reactive antibodies. *M. smegmatis* clones that are positive by colony blotting for Mtp will be confirmed by TEM and IF as previously described (69). Thus the expression and production of *M. tuberculosis* pili by *M. smegmatis* should be readily detectable by using these techniques. Plasmids from Mtp-positive clones will be isolated and the insert DNA will be characterized by restriction digest analysis to define the DNA regions that they contain.

Example 3

Defining the Relationship Between Expression of Pili and the Ability of *M. tuberculosis* to Adhere, Enter, and Survive Intracelluarly within Host Cells Background/Rationale.

In this experiment we are proposing to address specific questions regarding the biological function and role of Mtp in adherence and interaction of the bacteria with host epithelial cells and macrophages. We will also study other biological properties associated with well-characterized pili such as bacterial aggregation, erythrocyte agglutination, binding to extracellular matrix proteins, and the ability of Mtp to stimulate production of pro-inflammatory molecules.

1. Binding of Purified Mtp or Pilin Monomers to Host Cells.

We will also assess the ability of purified Mtp filaments, pilin monomers, or fluorescent-beads (0.5 um, Dynamics Corp., Portland, Oreg.) coated with these proteins and Mtp derived peptides to bind directly to cultured A549 cells, U-937 macrophages, or human macrophages. Mtp, pilin, or beads coated with these proteins, as indicated by the manufacturer's instructions, will be incubated with host cells (cultured on cover slips) for 4 h and then washed. Uncoated beads will be used as a control. The presence of fluorescent-beads will be observed directly by fluorescence microscopy, while bound pili or pilin will be detected by IF using affinity-purified anti-Mtp antibody followed by incubation with goat anti-rabbit IgG ALEXA FLUOR 488. Alternatively, Mtp fibers will be biotinylated with amino-sulfo-biotin (Pierce) and binding of the pili to host cells will be detected using streptavidin conjugated to ALEXA FLUOR 488 and fluorescence microscopy. These experiments will provide significant information regarding the direct role of Mtp in the interaction of *M. tuberculosis* with eukaryotic cells.

2. Effect of Specific Antibody Against Mtp.

Anti-Mtp antibody preparations will be added singly or in combination to the adherence assay, as described above, to determine what level of adherence to host cells is due to the adhesin. Preimmune rabbit serum, normal mouse serum, and buffer alone will be used as controls. By comparing the decrease in levels of bacteria associated with host cells caused by each antibody preparation we will be able to determine the level of attachment conferred by Mtp. It is anticipated that these experiments will help to differentiate the role of pili from known *M. tuberculosis* adhesins in the attachment to host cells and will potentially show that Mtp do play a role in adherence and are a viable target for developing a vaccine designed to prevent TB infection by blocking the adherence of Mtp and the bacteria to the cells in the human lung.

3. Interactions of Extracellular Matrix Proteins with *M. Tuberculosis* Pili.

Figure 5:
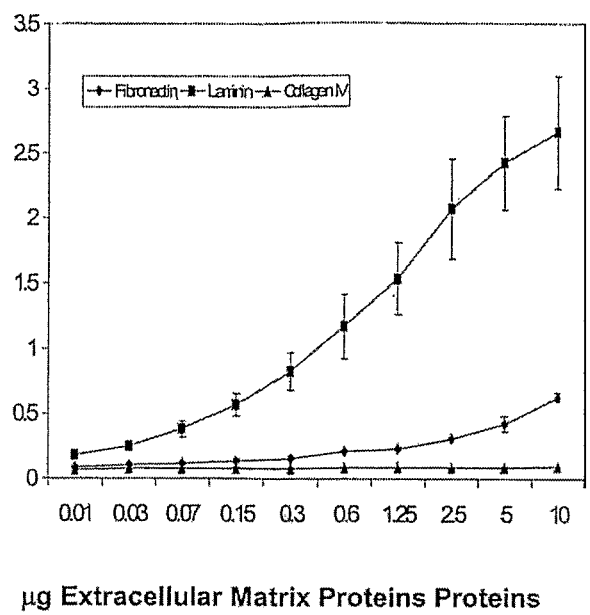
FIG. 5: Mtp binds to extracellular matrix proteins. Shown are the results of binding of increasing concentrations of fibronectin, laminin, and collagen type IV to Mtp-coated ELISA plates. Binding was quantitated by ELISA at $A_{450}$. Results are presented from 3 independent experiments run in triplicate.
Figure 6:
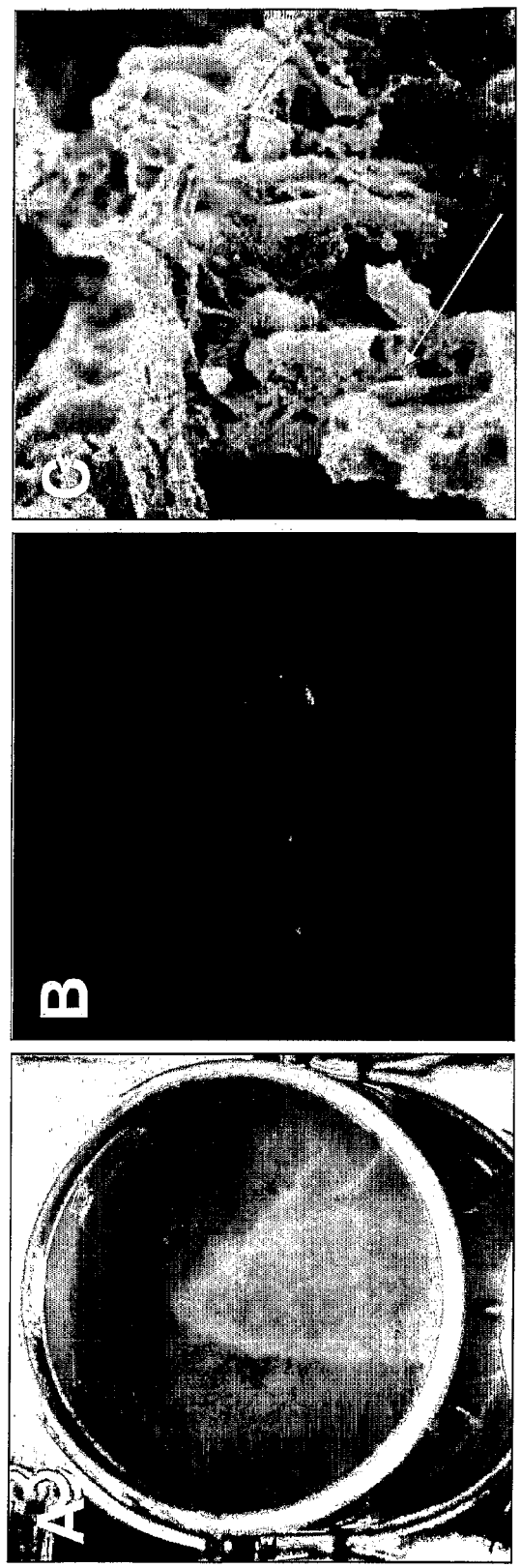
FIGS. 6A, 6B and 6C: Biofilm growth of *M. tuberculosis* H37Ra. The GFP expressing bacilli produce a film on the glass coverslip (A) shown by confocal microscopy in (B) and high resolution SEM in (C). Note the typical biofilm architecture in the low magnification reconstruction (B) and the Mtp fibers produced by the mycobacteria shown with arrow (C).
Figure 7:
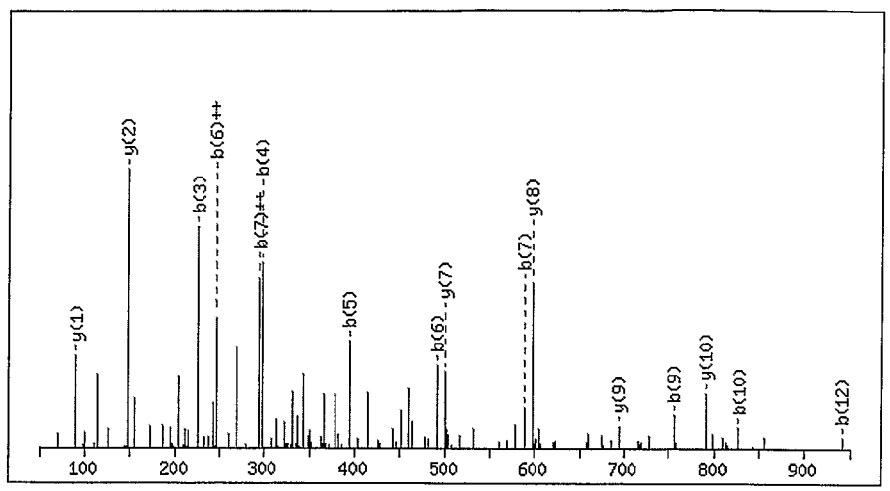
FIGS. 7A and 7B: Tandem mass spectroscopy fragmentation pattern of the acid hydrolysate produced from Mtp samples (A), actual identifications are indicated in red (bold) and theoretically possible fragments are black (B).
Figure 9:
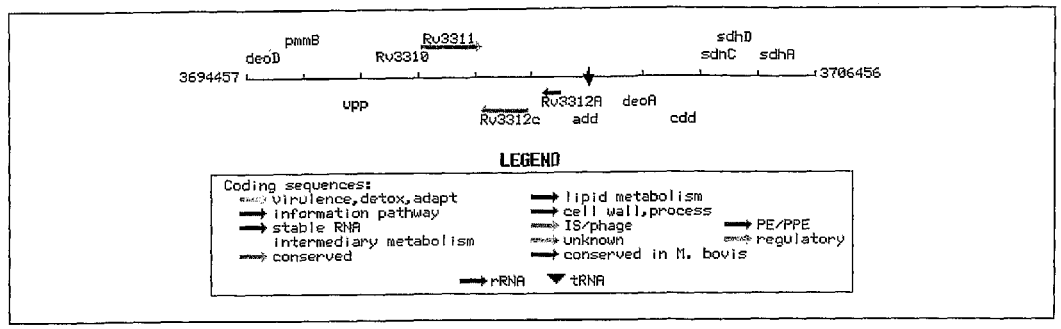
FIG. 9: Genome organization of putative mtpA region in *M. tuberculosis* H37Rv. The arrowhead denotes the ORF coding for the identified protein as described in the text. Display obtained at: http://genolist.pasteur.fr/TuberculList/.

Studies discussed above (see FIG. 5) demonstrate that Mtp binds to ECM, in particular to laminin in a dose-dependent manner. Laminin-binding proteins have been reported by others to be produced by *M. tuberculosis, M. leprae*, and *M. smegmatis* (43-45, 172). Our results strongly suggest that Mtp may act as a *M. tuberculosis* adhesin by allowing the microbe to attach to lung ECM to initiate adherence and colonization. Further studies on Mtp binding to ECM will be done to confirm and extend these initial observations.

Wells of microtiter plates will be coated with purified Mtp, His-tagged-MtpA pilin monomer, and Mtp peptides and blocked using Superblock (Pierce) as described above. Various human or mouse ECM will be added to coated wells including laminin, fibronectin, collagen IV, and virotnectin over a protein concentration of 0.01 µg/ml to 10 µg/ml per well. BSA will be added to wells as a negative control. ELISA plates will be incubated, washed, and bound ECM will be detected using specific anti-ECM antibodies (Sigma) and peroxidase conjugates as previously described. The ELISA assays will be read at $OD_{450}$ using a microtiter plate reader. These experiments will reconfirm our initial studies that Mtp binds to laminin and fibronectin and does not bind to collagen IV and will determine if Mtp binds to vitronectin.

Additionally, these studies will also determine whether ECM will bind to native Mtp, MtpA pilin monomer, as well as to Mtp peptides. By performing binding assays using Mtp peptides we may be able to determine which regions of Mtp protein are involved in adherence to ECM. To verify specificity of Mtp binding to ECM, anti-Mtp antibody, anti-MptA pilin, and anti-Mtp peptide antibodies will be used in the ELISA assays to block Mtp and Mtp protein derivatives from binding to ECM.

Assays to study the adherence of *M. tuberculosis* bacteria to ECM will also be done using the matrix proteins that are found to bind to Mtp by ELISA assays as described above. This bacterial adherence assay will be done following the method of Fink et al. (173). Twenty-four well tissue culture plates will be coated with ECM at 10 and 50 µg/ml. As controls, some wells will be untreated and others coated with BSA. Wild-type *M. tuberculosis*, pili mutant, and the complemented strains, all at $10^7$ bacteria per ml in HBSS, will be added to ECM-coated wells and incubated at 37° C. in a humidified $CO_2$ incubator for 1, 2 and 4 h. Wells will then be washed with HBSS at the various time points, bound bacteria will be recovered by treatment with one ml of 7H9 containing 1% TRITON-X-100, and viable plate counts will be determined. The percent adherence will be calculated by dividing the number of adherent CFU per well by the number of inoculated CFU. If Mtp play a role in binding to ECM, the pili mutant should bind at lower numbers than the parental or the complemented strain. To demonstrate the role of Mtp in binding to ECM in the assay, experiments will also be done using anti-Mtp antibody. If Mtp plays a role in binding to ECM, the presence of anti-Mtp in the assay will decrease the adherence of wild-type bacteria and the complemented strain to the ECM-coated wells. Alternatively, if problems arise with this methodology, ELISA plates coated with *M. tuberculosis* will be used to monitor binding of ECM as described by Marques et al. (172).

We anticipate that these proposed studies will confirm and extend the evidence that Mtp binds to laminin and fibronectin and perhaps other ECM. Such results would suggest that binding of *M. tuberculosis* to ECM via Mtp might play a critical role in the microbes' ability to colonize and possibly disseminate within the human host.

4. Evaluating Whether *M. Tuberculosis* Pili Stimulate Production of Pro-Inflammatory Cytokines.

In human tuberculosis the host mounts a cell-mediated immune response to the infection which leads to the recruitment and activation of macrophages and T cells (122). The microbes' ability to survive this response culminates in the development of a granulomatous lesion to contain and wall off the bacterial infection (122). Bacterial-host cell interactions lead to the induction and release of various proinflammatory mediators by both macrophages and resident epithelial cells in response to the infection. It has been reported that some bacterial products including LPS, flagella, and pili from different microbial pathogens induce secretion of a variety of proinflammatory cytokines (123, 124,161,162). We are interested in determining if Mtp causes release of proinflammatory cytokines by both human macrophages and A549 alveolar epithelial cells in response to *M. tuberculosis* pili. Previous studies by Bermudez et al. reported that after infection with *M. tuberculosis*, A549 cells were stimulated to secrete various cytokines (38).

Monolayers of both cell types will be prepared in 24-well tissue culture plates as previously described and various concentrations of purified Mtp (1, 10, 50, and 100 µg/ml) will be added to the monolayers for 1, 2, 4, 8, 16, or 24 h. Cell culture supernatant will be isolated at these time points and frozen at −70° C. until use for determination of cytokine levels. Secretion of cytokines IL-1α, IL-6, and IL-8 will be determined using ELISA sandwich immunosorbent assays (R & D Systems or Biosource International). The cytokine bead array technique (BD Bioscience) will be used to evaluate the presence of cytokines IFN-γ, TNF-α, IL-2, 4, 5, and 10 simultaneously (125). The cytokine bead array assay will be performed according to the manufacturer's instructions. Briefly, antibodies against each of the above cytokines are provided coated onto six different groups of beads that differ in their fluorescence intensity. The beads are mixed together with a second group of cytokine specific antibodies conjugated to phycoerytlirin. Supernatants from the pili-treated macrophages and A549 cells will be added to the bead antibody mixture and incubated for 3 hours at room temperature. The beads will be washed and analyzed by flow cytometry using a BD FacScan flow cytometer. Concentrations of each cytokine will be determined based on known amounts of standard cytokine added to a set of control beads. Monolayers incubated with buffer only and host cells treated with PPD (Mycos Research) at 1 and 10 μg/ml, will be used as negative and positive controls, respectively. It is anticipated that Mtp will influence the production of proinflammatory cytokines by both human macrophages and A549 epithelial cells. If positive results are obtained using Mtp then the ability of wild-type *M. tuberculosis* and the pili mutant will be tested in the assay to determine if a difference in cytokine release is observed. Such results would suggest that Mtp potentially could be an early antigen sensed by the host to respond to and modulate the immune response to a tuberculosis infection.

Example 4

Evaluation of the Protective Efficacy of a Mtp Vaccine

Background/Rationale.

Mice immunized with Mtp should produce humoral and cellular anti-tuberculosis responses and would be protected against experimental TB in comparison to naïve mice. These studies will investigate the potential protective properties of Mtp against tuberculosis infections using a mouse respiratory aerosol model (126-128).

1. Evaluation of the Protective Efficacy of *M. Tuberculosis* Pili Against Aerosol Challenge.

Survival studies will be done to evaluate whether Mtp can stimulate a protective immune response in mice against a *M. tuberculosis* aerosol challenge. Groups of C57BL/6 mice (10 mice each) will be immunized via the subcutaneous route with purified Mtp at 10, 50 or 100 μg in Freunds incomplete adjuvant and then given two additional boosters at the same antigen concentration at two week intervals. After Mtp immunization, sera will be obtained from mice and tested in ELISA for the presence of anti-Mtp titers to verify that the vaccination regimen has stimulated an immune response in the animals. If need be, animals will be immunized longer to induce at least a strong humoral immune response. As a positive control, a group of mice will be vaccinated subcutaneously with $5 \times 10^6$ CFU of *M. bovis* BCG Pasteur (127, 128), while a negative control group will only be treated with buffer injections. Mtp-vaccinated mice will be challenged by the aerosol route, two weeks after receiving their final booster, while mice vaccinated with BCG will be infected six weeks after immunization. Mice will be infected with 50 to 100 CFU of *M. tuberculosis* H37Rv via the aerosol route using a Middlebrook chamber as described above. Mice will be maintained until they become moribund and then they will be euthanized. Survival of vaccinated and control mice will be monitored and tabulated over a 400 day period. If the *M. tuberculosis* pili stimulate a protective immune response in mice, then one should observe a significant extension of survival time as compared to the unimmunized control mice. It will be interesting to compare the survival rate of the Mtp vaccine group as compared to the BCG vaccine group, since BCG is a standard vaccine that gives excellent protection in mice against an *M. tuberculosis* aerosol challenge (127, 128).

2. Evaluation of the Immune Response to Mtp Vaccination.

If Mtp vaccination is found to significantly protect mice against an aerosol TB infection, then further studies will be done to investigate the protective immune response that was induced by this antigen. To do this, the humoral and cellular immune responses in Mtp-vaccinated mice and a vaccinated group challenged with TB will be studied.

Mice will be vaccinated with the optimal dose of Mtp as determined in the protection studies described above. Control mice will be given buffer only, while another group of mice will be immunized with BCG and used as a positive control in these studies. These three groups of mice will then be sacrificed 30 days after their last vaccination. Another set of vaccinated animals will be aerosol challenged with *M. tuberculosis* H37Rv and sacrificed 5 and 6 weeks later. Before death, blood will be recovered via bleeding from the orbital plexus of mice and sera will be isolated. Anti-Mtp antibody titers will be determined via ELISA assays as described above. Levels of total IgG as well as levels of IgG1 and IgG2a isotypes will be measured to determine whether Mtp induces either a Th1 or Th2-type immune response (129).

In order to determine whether Mtp vaccination stimulates a cell-mediated immune response, cytokine responses of mouse splenocytes will be determined using ex vivo analysis (134). Spleens from 5 mice from each study group described above will be pooled, and lymphocytes purified over a FICOLL-HYPAQUE gradient. CD3-positive T-cells will be enriched using a T-cell enrichment column (R & D Systems) following the procedure of Kobie et al. (134). Thymocytes will be re-stimulated in vitro using Mtp antigen or PPD pulsed bone marrow derived dendritic cells [DC] (134). These DC cultures will be prepared and matured with TNF-α as previously described (134). The DC will be primed 24 h before incubation with splenocytes by the addition of 1 or 10 μg Mtp, 1 or 10 μg of PPD (Mycos Research), or buffer alone. Controls will include DC alone and T cells alone. Supernatants will be collected after 72 h, and the levels of IFN-γ, IL-4, and IL-10 secretion will be determined by ELISA using immunoglobulin specific for mouse cytokines (PharMingen). IFN-γ cytokine production has been demonstrated to be critical in the development of a protective anti-mycobacterial immune response. Th1-type cytokines, such as IFN-γ, are critical in preventing active TB disease (122). IL-4 and IL-10 cytokine production is normally induced during a Th2-type immune response which is not optimal for control of tuberculosis infections (122, 135, 136). Thus, by monitoring the level of IFN-γ, IL-4, and IL-10 cytokine secretion in these assays we will be able to elucidate what type of cell-mediated immune response Mtp antigen induces in mice. These results will be compared to levels of cellular immunity (cytokine production) induced after TB infection of Mtp-vaccinated, BCG vaccinated, and control mice, as described above, either 7 or 14 d after aerosol challenge.

Animal studies will also be done to determine whether immunization with Mtp restricts the growth of *M. tuberculosis* in the lungs and spleens of aerosol-infected mice. Thirty days after vaccination with Mtp, BCG, or unimmunized control mice will be infected with virulent *M. tuberculosis* as described above. Numbers of viable bacilli will be determined in lungs and spleens of these mice at 4, 9, and 16 weeks after infection by plate count determinations, while histological analysis of mouse lungs will also be done as previously described. To inhibit growth of BCG from BCG-vaccinated mice and not *M. tuberculosis*, samples will be plated on 7H11-OADC agar plates containing 2-thiophenecarboxylic acid hydrazide (2 μg/ml). This compound inhibits replication of BCG while not inhibiting growth of *M. tuberculosis* (127). If Mtp vaccination is protective, lower numbers of bacteria should be recovered from the lungs and spleens of infected animals and lung pathology should be decreased as compared to the unimmunized control mice. The BCG vaccine group will be a good comparative model in these studies since it has been shown that this attenuated, live vaccine decreases mycobacterial numbers and decreases observed lung pathology in mice (127, 128).

REFERENCES

1. Barnes, P. F., A. B. Bloch, P. T. Davidson, and D. E. Snider, Jr. 1991. Tuberculosis in patients with human immunodeficient virus infection. N. Engl. J. Med. 324:1644-1650.
2. Bloom, B. 1992. On the track of "killer" TB. Science. 255:148-150.
3. Schlesinger, L. S., C. G. Bellinger-Kawahara, N. R. Payne, and M. A. Horwitz. 1990. Phagocytosis of *Mycobacterium tuberculosis* is mediated by human monocyte complement receptors and complement component C3. J. Immunol. 144:2771-2780.
4. Armstrong, J. A., and P. D. Hart. 1971. Response of cultured macrophages to *Mycobacterium tuberculosis*, with observations on fusion of lysosomes and phagosomes. J. Exp. Med. 134:713-740.
7. Crowle, A. J., R. Dahl, E. Ross, and M. H. May. 1991. Evidence that vesicles containing living, virulent *Mycobacterium tuberculosis* or *Mycobacterium avium* in cultured human macrophages are not acidic. Infect. Immun. 59:1823-1831.
8. Collins, F. A. 1993. Tuberculosis: The return of an old enemy. Critical Rev. Microbiology. 19:1-16.
9. Dye, C., S. Scheele, V. Pathania, and M. C. Raviglione. 1999. Global Burden of tuberculosis: Estimated increase, prevalence, and mortality by country. JAMA. 282: 677-686.
10. Kaufmann, S. H. E., and D. B. Young. 1992. Vaccination against tuberculosis and leprosy. Immunobiology. 184:208-229.
11. Hirsch, C. S., J. J. Ellner, D. G. Russell, and E. A. Rich. 1994. Complement receptor-mediated uptake and tumor necrosis factor-a-mediated growth inhibition of *Mycobacterium tuberculosis* in human alveolar macrophages. J. Immunol. 152:743-753.
12. Kang, B. K., and L. S. Schlesinger. 1998. Characterization of mannose receptor-dependent phagocytosis mediated by *Mycobacterium tuberculosis* lipoarabinomannan. Infect. Immun. 66:2769-2777.
13. Sturgill-Koszycki, et al. 1994. Lack of acidification in *Mycobacterium* phagosomes produced by exclusion of vesicular proton-ATpase. Science 263:678-681.
14. Russell, D. G., S. Sturgill-Koszycki, T. Vanheyningen, H. Collins, and U. E. Schaible. 1997. Why intracellular parasitism need not be a degrading experience for *Mycobacterium*. Phil. Trans. R. Soc. Lond. B. 352: 1330-1310.
15. Deretic, V., and R. A. Fratti. 1999. *Mycobacterium tuberculosis* phagosome. Mol. Microbiol. 31: 1603-1609.
16. Riley, L. W. 1995. Determinants of cell entry and intracellular survival of *Mycobacterium tuberculosis*. Trends Microbiol. 3:27-31.
17. McDonough, K. A., Y. Kress, and B. R. Bloom. 1993. Pathogenesis of tuberculosis: Interaction of *Mycobacterium tuberculosis* with macrophages. Infect. Immun. 61:2763-2773.
18. Myrvik, Q. N., E. S. Leake, and M. J. Wright. 1984. Disruption of phagosomal membranes of normal alveolar macrophages by the H37Rv strain of *M. tuberculosis*. A correlate of virulence. Am. Rev. Respir. Dis. 129:322-328.
19. Dannenberg, A. M., Jr. 1991. Delayed-type hypersensitivity and cell-mediated immunity in the pathogenesis of tuberculosis. Immunol. Today 12:228-233.
20. Goren, M. B., O. Brokl, and W. B. Schaefer. 1974. Lipids of putative relevance to virulence of *Mycobacterium tuberculosis*: correlation of virulence with elaboration of sulfatides and strongly acidic acids. Infect. Immun. 9:142-149.
21. Chan, J., X. Fan, S. W. Hunter, P. J. Brennan, and B. R. Bloom. 1991. Lipoarabinomannan, a possible virulence factor involved in persistence of *Mycobacterium tuberculosis* within macrophages. Infect. Immun. 59:1755-1761.
22. Fratti, R. A., J. Chua, I. Vergne, and V. Deretic. 2003. *Mycobacterium tuberculosis* glycosylated phosphatidylinositol causes phagosome maturation arrest. PNAS. 100: 5437-5442.
23. Young, D. B., and S. T. Cole. 1993. Leprosy, tuberculosis, and new genetics. J. Bacteriol. 175:1-6.
24. Zhang, Y., B. Heym, B. Allen, D. B. Young, and S. T. Cole. 1992. The catalase-peroxidase gene and isoniazid resistance of *Mycobacterium tuberculosis*. Nature. 358:591-593.
25. Harris, P., and P. Ralph. 1985. Human leukemic models of myelomonocytic development: review of the HL-60 and U-937 cell lines. J. Leuk. Biol. 37: 407-422.
26. Wei, J., J. L. Dahl, J. W. Moulder, E. A. Roberts, P. O'Gaora, D. B. Young, and R. L. Friedman. 2000. Identification of a *Mycobacterium tuberculosis* gene that enhances mycobacterial survival in macrophages. J. Bacteriol. 182: 377-384.
27. Friedman, R. L., K. Nordensson, L. Wilson, E. T. Akporiaye, and D. E. Yocum. 1992. Uptake and intracellular survival of Bordetellapertussis in human macrophages. Infect. Immun. 60:4578-4585.
28. Nakagawara, A. and C. F. Nathan. 1983. A simple method for counting adherent cells: application to cultured monocytes, macrophages, and multinucleated giant cells. J. Immunol. Methods 56: 261-268.
29. Cole, S. T. et al. 1998. Deciphering the biology of *Mycobacterium tuberculosis* from the complete genome sequence. Nature 393: 537-544.
30. Fleishcmann, R. D. et al. 2002. Whole-genome comparison of *Mycobacterium tuberculosis* clinical and laboratory strains. J. Bacteriol. 185:5479-5490.
31. Smith, I. 2003. *Mycobacterium tuberculosis* pathogenesis and molecular determinants of virulence. Clin. Microbiol. Rev. 16: 463-496.
32. Schlesinger, L. S., S. R. Hull, and T. M. Kaufman. 1994. Binding of the terminal mannosyl units of lipoarabinomannan from a virulence strain of *Mycobacterium tuberculosis* to human macrophages. J. Immunol. 152:4070-4079.
33. Schlesinger, L. S., T. M. Kaufman, S. Iyer, S. R. Hull, and L. K. Marchiando. 1996. Differences in mannose receptor-mediated uptake of lipoarabinomannan from virulence and attenuated strains of *Mycobacterium tuberculosis* by human macrophages. J. Immunol. 157:4568-4575.
34. Crystal, R. J. 1991. Alveolar macrophages, p. 527-528. In R. J. Crystal and J. B. West (ed.), The lung: scientific foundations. Raven Press, New York, N.Y.

35. Bermudez, L. E., and Goodman. 1996. *Mycobacterium tuberculosis* invades and replicates within type II alveolar cells. Infect. Immun. 64:1400-1406.
36. Lin, Y., M. Zhang, and P. F. Barnes. 1998. Chemokine production by a human alveolar epithelial cell line in response to *Mycobacterium tuberculosis*. Infect. Immun. 66:1121-1126.
37. Mehta, P. K., C. H. King, E. M. White, J. J. Murtagh, and F. D. Quinn. 1996. Comparison of in vitro models for the study of *Mycobacterium tuberculosis* invasion and intracellular replication. Infect. Immun. 64:2673-2679.
38. Bermudez, L. E., F. J. Sangari, P. Kolonoski, M. Petrofsky, and J. Goodman. 2002. The efficiency of the translocation of *Mycobacterium tuberculosis* across a bilayer of epithelial and endothelial cells as a model of the alveolar wall is a consequence of transport within mononuclear phagocytes and invasion of alveolar epithelial cells. Infect. Immun. 70:140-146.
39. Pessolani, M. C. V., M. A. de M. Marques, V. M. Reddy, C. Locht, and F. D. Menozzi. 2003. Systemic dissemination in tuberculosis and leprosy: do mycobacterial adhesins play a role? Microbes Infect. 5: 677-684.
40. F. D. Menozzi, J. H. Rouse, M. Alavi, M. Laude-Sharp, J. Muller, R. Bischoff, M. J. Brennan, and C. Locht. 1996. Identification of a heparin-binding hemagglutinin present in mycobacteria. J. Exp. Med. 184:993-1001.
41. Menozzi, F. D., R. Bischoff, E. Fort, M. J. Brennan, and C. Locht. 1998. Molecular characterization of the mycobacterial heparin-binding hemagglutinin, a mycobacterial adhesin. PNAS. 95: 12625-12630.
42. Pethe, K., S. Alonso, F. Biet, G. Delogu, M. J. Brennan, C. Locht, and F. D. Menozzi. 2001. The heparin-binding haemagglutinin of *M. tuberculosis* is required for extrapulmonary dissemination. Nature. 412:190-194.
43. Pethe, K., V. Puech, M. Daffe, C. Josehans, H. Drobecq, C. Locht, and F. D. Menozzi. 2001. *Mycobacterium smegmatis* lamin-binding glycoprotein shares epitopes with *Mycobacterium tuberculosis* heparin-binding haemagglutinin. Mol. Microbiol. 39:89-99.
44. Prabhakar, S., P. S. Annapurna, N. K. Jain, A. B. Dey, J. S. Tyagi, and H. K. Prasad. 1998. Identification of an immunogenic histone-like protein of *Mycobacterium tuberculosis*. Tuber. Lung Dis. 79:43-53.
45. Shimoji, Y., V. Ng, K. Matsumura, V. A. Fischetti, and A. Rambukkana. 1999. A 2I-kDa surface protein of *Mycobacterium leprae* binds to peripheral nerve laminin-2 and mediates Schwann cell invasion. PNAS. 96:9857-9862.
46. Middleton, A. M., M. V. Chadwick, A. G. Nicholsin, A. Dewar, R. K. Groger, E. J. Brown, T. L. Ratliff, and R. Wilson. 2002. Interaction of *Mycobacterium tuberculosis* with human respiratory mucosa. Tuberculosis. 82:69-78.
47. Middleton, A. M., M. V. Chadwicj, A. G. Nicholson, A. Dewar, C. Feldman, and R. Wilson. 2003. Investigation of mycobacterial colonization and invasion of the respiratory mucosa. Thorax. 58:246-251.
48. Abou-Zeid, C., T. Garbe, R. Latigra, H. G. Wiker, M. Harboe, G. A. Rook, and D. Young. 1991. Genetic and immunological analysis of *Mycobacterium tuberculosis* fibronectin-binding proteins. Infect. Immun. 59:2712-2718.
49. Costerton, J. W., P. S. Stewart, and E. P. Greenberg. 1999. Bacterial biofilms: A common cause of persistent infections. Science 284:1318-1322.
50. Brennan, M. J., and G. Delogu. 2002. The PE multigene family: a molecular mantra for mycobacteria. Trends Microbiol. 10:246-249.
51. Banu, S., N. Honore, B. Saint-Joanis, D. Philpott, M. C. Prevost, and S. T. Cole. 2002. Are the PE-PGRS proteins of *Mycobacterium tuberculosis* variable surface antigens? Mol. Microbiol. 22:9-19.
52. Ramakrishnan, L., N. A. Federspiel, and S. Falkow. 2000. Granuloma-specific expression of *mycobacterium* virulence proteins from the glycine-rich PE-PGRS family. Science. 288:1436-1439.
53. Brennan, M. J., G. Delogu, Y. Chen, S. Bardarov, J. Kriakov, M. Alavi, and W. R. Jacobs, Jr. 2001. Evidence that mycobacterial PE_PGRS proteins are cell surface constituents that influence interactions with other cells. Infect. Immun. 69:7326-7333.
54. Espitia, E., J. P. Lacletee, M. M. Palmino, A. Amador, J. Campuzano, A. Martens, M. Singh, R. Cicero, Y. Zhang, and C. Moreno. 1999. The PE-PGRS glycine-rich proteins of *Mycobacterium tuberculosis*: a new family of fibronectin-binding proteins? Microbiol. 145:3487-3495.
55. Delogu, G., and M. J. Brennan. 2001. Comparative immune response to PE and PE_PGRS antigens of *Mycobacterium tuberculosis*. Infect. Immun. 69:5606-5611.
56. Stone, B. J., and Y. Abu Kwaik. 1998. Expression of multiple pili by *Legionella pneumophila*: Identification and characterization of a type IV pilin gene and its role in adherence to mammalian and protozoan cells. Infect Immun. 66:1768-1775.
57. Fullner, K. J., and J. J. Mekalanos. 1999. Genetic characterization of a new type IV-A pilus gene cluster found in both classical and el tor biotypes of *Vibrio cholerae*. Infect. Immun. 67:1393-1404.
58. Takayama, K., H. K. Schnoes, E. L. Armstrong, and R. W. Boyle. 1975. Site of inhibitory action of isoniazid in the synthesis of mycolic acids in *Mycobacterium tuberculosis*. J. Lipid Res. 16:308-317.
59. Old, D. C. and J. P. Duguid. 1970. Selective outgrowth of fimbriate bacteria in static liquid medium. J. Bacteriol. 103:447-456.
60. Tacket, C. O., Maneval, D. R., and Levine, M. M. (1987) Purification, morphology, and genetics of a new fimbrial putative colonization factor of enterotoxigenic *Escherichia coli* O159:H4. Infect. Immun. 55: 1063-1069.
61. Collinson, S. K., L. Emody, K. H. Müller, T. J. Trust, and W. W. Kay. 1991. Purification and characterization of thin, aggregative fimbriae from *Salmonella enteritidis*. J. Bacteriol. 173:4773-4781.
62. Karch, H., H. Leying, K. H. Buscher, H. P. Kroll, and W. Opferkuch. 1985. Isolation and separation of physicochemically distinct fimbrial types expressed on a single culture of *Escherichia coli* O7:K1:H6. Infect. Immun. 47:549-554.
63. Eshdat, Y., F. J. Silverblatt, and N. Sharon. 1981. Dissociation and reassembly of *Escherichia coli* type 1 pili. J. Bacteriol. 148:308-314.
64. Hanson, M. S., J. Hempel, and C. C. Brinton, Jr. 1988. Purification of the *Escherichia coli* type 1 pilin and minor pilus proteins and partial characterization of the adhesin protein. J. Bacteriol. 170:3350-3358.
65. Fader, R. C., L. K. Duffy, C. P. Davis, and A. Kurosky. 1982. Purification and chemical characterization of type 1 pili isolated from *Klebsiella pneumoniae*. J. Biol. Chem. 257:3301-3305.
66. Lévesque, C., C. Vadeboncoeur, F. Chandad, and M. Frenette. 2001. *Streptococcus salivarius* fimbriae are composed of a glycoprotein containing a repeated motif assembled into a filamentous nondissociable structure. J. Bacteriol. 183:2724-2732.

67. Ortalo-Magné, A., A. Lemassu, M. A. Lanéelle, F. Bardou, G. Silve, P. Gounon, G. Marchal, and M. Daffé. 1996. Identification of the surface-exposed lipids on the cell envelopes of *Mycobacterium tuberculosis* and other mycobacterial species. J. Bacteriol. 178:456-461.
68. Girón, J. A., M. M. Levine, and J. B. Kaper. 1994. Longus: a long pilus ultrastructure produced by human enterotoxigenic *Escherichia coli*. Mol. Microbiol. 12:71-82.
69. Giron, J. A., A. G. Torres, E. Freer, and J. B. Kaper. 2002. The flagella of enteropathogenic *Escherichia coli* mediate adherence to epithelial cells. Mol. Microbiol. 44:361-379.
70. Zhang, X., I. S. Tsui, C. M. Yip, A. W. Fung, D. Wong, X. Dai, Y. Yang, J. Hackett, and C. Morris. 2000. *Salmonella enterica* serovar Typhi used type IV-B pili to enter human intestinal epithelial cells. Infect. Immun. 68:3067-3073.
71. Nika, J. R., J. L. Latimer, C. K. Ward, R. J. Blick, N. J. Wagner, L. D. Cope, G. G. Maharias, R. S. Munson Jr., and E. J. Hansen. 2002. *Haemophilus ducreyi* requires the flp gene cluster for microcolony formation In Vitro. Infect. Immun. 70:2965-2975.
72. Mu, X., E. H. Egelman, and E. Bullitt. 2002. Structure and function of Hib pili from *Haemophilus influenzae* type b. J. Bacteriol. 184:4868-4874.
73. Torres, A. G., J. A. Girón, N. T. Perna, V. Burland, F. R. Blattner, F. Avelino-Flores, and J. B. Kaper. 2002. Identification and characterization of lpfABCC'DE, a fimbrial operon of enterohemorrhagic Eshericia coli O157:H7. Infect. Immun. 70:5416-5427.
74. Yanagawa, R., and E. Honda. 1976. Presence of pili in species of human and animal parasites and pathogens of the genus *Corynebacterium*. Infect. Immun. 13:1293-1295.
75. Yanagawa, R., and K. Otsuki. 1970. Some properties of the pili of *Corynebacterium* renale. J. Bacteriol. 101:1063-1069.
76. Honda, E., and R. Yanagawa. 1974. Agglutination of trypsinized sheep erythrocytes by the pili of *Corynebacterium renale*. Infect. Immun. 10:1426-1432.
77. Mattos-Guaraldi, A. L., L. Formiga, and G. A. Pereira. 2000. Cell surface components and adhesion in *Corynebacterium diphtheriae*. Microbes Infect. 2:1507-1512.
78. Colombo, A. V., R. Hirata Jr., C. M. R. de Souza, L. Monteiro-Leal, J. O. Previato, L. Formiga, A. Andrade, and A. L. Mattos-Guaraldi. 2001. *Corynebacterium diphtheriae* surface proteins as adhesins to human erythrocytes. FEMS Microbiol. Lett. 197: 235-239.
79. Fenno, J. C., D. J. LeBlanc, and P. Fives-Taylor. 1989. Nucleotide sequence analysis of a type 1 fimbrial gene of *Streptococcus sanguis* FW213. Infect. Immun. 57:3527-3533.
80. Froeliger, E. H., and P. Fives-Taylor. 2001. *Streptococcus parasanguis* fimbria-associated adhesin Fap1 is required for biofilm formation. Infect. Immun. 69:2512-2519.
81. Burnette-Curley, D., V. Wells, H. Viscount, C. L. Munro, J. C. Fenno, P. Fives-Taylor, and F. L. Marcina. 1995. FimA, a major virulence factor associated with *Streptococcus parasanguis* endocarditis. Infect. Immun. 63:4669-4674.
82. Gibbons, R. J., D. I. Hay, J. O. Cisar, and W. B. Clark. 1988. Adsorbed salivary proline-rich protein 1 abd statherin: receptors for type 1 fimbriae of *Actinomyces viscous* T14V-J1 on apatitic surfaces. Infect. Immun. 56:2990-2993.
83. Cisar, J. O. 1986. Fimbrial lectins of the oral *actinomyces*, p. 183-196. In D. Mirelman (ed.), Microbial lectins and agglutinins: properties and biological activity. John Wiley & Sons, Inc. New York, N.Y.
84. Yeung, M. K., B. M. Chassy, and J. O. Cisar. 1987. Cloning and expression of a type 1 fimbrial subunit of *Actinomyces viscous* T14V. J. Bacteriol. 169:1678-1683.
85. Yeung, M. K., and J. O. Cisar. 1988. Cloning and nucleotide sequence of a gene for *Actinomyces naeslundii* WVU45 type 2 fimbriae. J. Bacteriol. 170:3803-3809.
86. Yeung, M. K., and J. O. Cisar. 1990. Sequence homology between the two subunits of two immunologically and functionally distinct types of fimbriae of *Actinomyces* ssp. J. Bacteriol. 172:2462-2468.
87. Yeung, M. K., and P. A. Ragsdale. 1997. Synthesis and function of *Actinomyces naeslundii* T14V type 1 fimbriae require the expression of additional fimbria-associated genes. Infect. Immun. 65:2629-2639.
88. Kachlany, S. C., P. J. Planet, M. K. Bhattacharjee, E. Kollia, R. DeSalle, D. H. Fine, and D. H. Figurski. 2000. Nonspecific adherence by *Actinobacillus actinomycetemcomitans* requires genes widespread in bacteria and archaea. J. Bacteriol. 182:6169-6176.
89. Kachlany, S. C., P. J. Planet, R. DeSalle, D. H. Fine, D. H. Figurski, and J. B. Kaplan. 2001. flp-1, the first representatitive of a new pilin gene subfamily, is required for nonspecific adherence of *Actinobacillus actinomycetemcomitans*. Mol. Microbiol. 40:542-554.
90. Jacobs, W. R., Jr., G. V. Kalpana, J. D. Cirillo, L. Pascopella, S. B. Snapper, R. A. Udani, W. Jones, R. G. Barletta, and B. R. Bloom. 1991. Genetic systems for mycobacteria. Methods Enzymol. 204: 537-555.
91. Ramakrishnan, L., and S. Falkow. 1994. *Mycobacterium marinum* persists in cultured mammalian cells in a temperature-restricted fashion. Infect. Immun. 62:3222-3229.
92. Menozzi, F. D., P. E. Boucher, G. Riveau, C. Gantiez, and C. Locht. 1994. Surface-associated filamentous hemagglutinin induces autoagglutination of *Bordetella pertussis*. Infect. Immun. 62:4261-4269.
93. Chang, S. L., R. K. Taylor, M. Koomey, and J. J. Mekalanos. 1995. Single amino acid substitutions in the N-terminus of Vibro cholerae TcpA affects colonization, autoagglutination, and serum resistance. Mol. Microbiol. 17:1133-1142.
94. Bermudez, L. E., and J. Goodman. 1996. *Mycobacterium tuberculosis* invades and replicates within type II alveolar cells. Infect. Immun. 64:1400-1406.
95. Shepard, C. C. 1957. Growth characteristics of tubercle bacilli and certain other mycobacteria in HeLa cells. J. Exp. Med. 105:39-55.
96. Zhang, M., K. J. Kim, D. Iyer, Y. Li, J. Belisle, K. McEnery, E. D. Crandall, and P. F. Barnes. 1997. Effects of *Mycobacterium tuberculosis* on the bioelectric properties of the alveolar epithelium. Infect. Immun. 65:692-698.
97. Finlay, B. B. and S. Falkow. 1997. Common themes in microbial pathogenicity revisited. Microbiol. Mol. Biol. Rev. 61:136-169.
98. Cossart, P. 2002. Molecular and cellular basis of the infection by *Listeria monocytogenes*: an overview. Int. J. Med. Microbiol. 291:401-409.
99. Donnenberg, M. S. 2000. Pathogenic strategies of enteric bacteria. Nature 406:768-774.
100. Klemm, P., and M. A. Schembri. 2000. Bacterial adhesins: function and structure. Int. J. Med. Microbiol. 290: 27-35.
101. Strom, M. S. and S. Lory. 1993. Structure-function and biogenesis of the type IV pili. Ann. Rev. Microbiol. 47: 565-596.
102. Gaastra, W. and A. M. Svennerholm. 1996. Colonization factors of human enterotoxigenic *Escherichia coli* (ETEC). Trends Microbiol. 4: 444-452.

103. Taylor, R. K., V. L. Miller, D. B. Furlong and J. J. Mekalanos. 1987. Use of phoA gene fusions to identify a pilus colonization factor coordinately regulated with cholera toxin. PNAS 84:2833-2837.

104. Girón, J. A., A. S. Y. Ho, and G. K. Schoolnik. 1991. An inducible bundle-forming pilus of enteropathogenic *Escherichia coli*. Science 254:710-713.

105. Girón, J. A., A. S. Y. Ho and G. K. Schoolnik. 1993. Characterization of fimbriae produced by enteropathogenic *Escherichia coli*. J. Bacteriol. 175: 7391-7403.

106. Mulvey, M. A. Adhesion and entry of uropathogenic *Escherichia coli*. 2002. Cell. Microbiol. 4:257-271.

107. Smyth, C. J., M. B. Marron, J. M. Twohig and S. G. Smith. 1996. Fimbrial adhesins: similarities and variations in structure and biogenesis. FEMS Immunol. Med. Microbiol. 16:127-139.

108. Thanassi, D. G., E. T. Saulino and S. J. Hultgren. 1998. The chaperone/usher pathway: a major terminal branch of the general secretory pathway. Curr. Op. Microbiol. 1:223-231.

109. Bieber, D., S. W. Ramer, C. Y. Wu, W. J. Murray, T. Tobe, R. Fernández, and G. K. Schoolnik, G. K. 1998. Type IV pili, transient bacterial aggregates, and virulence of enteropathogenic *Escherichia coli*. Science 280:2114-2118.

110. Skerker, J. M. and H. C. Berg. 2001. Direct observation of extension and retraction of type IV pili. PNAS 98:6901-6904.

111. Olsén, A., A. Jonsson and S. Normak. 1989. Fibronectin binding mediated by a novel class of surface organelles on *Escherichia coli*. Nature 338:652-656.

112. Olsén, A., M. Wick, M. Morgelin and L. Bjorck. 1998. Curli, fibrous surface proteins of *Escherichia coli*, interact with major histocompatibility complex class 1 molecules. Infect. Immun. 66:944-949.

113. Chapman, M. R., L. S. Robinson, J. S. Pinkner, R. Roth, J. Heuser, M. Hammar, S. Normark and S. J. Hultgren. 2002. Role of *Escherichia coli* curli operons in directing amyloid fiber formation. Science 295:851-855.

114. Prigent-Combaret, C., E. Brombacher, O. Vidal, A. Ambert, P. Lejeune, P. Landini and C. Dorel. 2001. Complex regulatory network controls initial adhesion and biofilm formation in *Escherichia coli* via regulation of the csgD gene. J. Bacteriol. 183:7213-7223.

115. Laemmli, U. K. 1970. Cleavage of structural proteins during the assembly of the head of bacteriophage T4. Nature 227:680-685.

116. McMichael, J. C. and J. T. Ou. 1979. Structure of common pili from *Escherichia coli*. J. Bacteriol. 139:969-975.

117. Evans, D. G., D. J. Evans and W. Tjoa. 1977. Hemagglutination of human group A erythrocytes by enterotoxigenic *Escherichia coli* isolated from adults with diarrhea: correlation with colonization factor. Infect. Immun. 18:330-337.

118. De Sousa-D'Auria, C., R. Kacem, V. Puech, M. Tropis, G. Leblon, C. Houssin, and M. Daffe. 2003. New insights into the biogenesis of the cell envelope of corynebacteria: identification and functional characterization of five new mycoloyltransferase genes in *Corynebacterium glutamicum*. FEMS Microbiol. Lett. 224:35-44.

119. Stephenson, A. E., H. Wu, J. Novak, M. Tomana, K. Mintz, and P. Fives-Taylor. 2002. The Fap1 fimbrial adhesion is a glycoprotein: antibodies specific for the glycan moiety block the adhesion of *Streptococcus parasanguis* in an in vitro tooth model. Mol. Microbiol. 43:147-157.

120. Aas, F. E., M. Wolfgang, S. Frye, S. Dunham, C. Lovold, and M. Koomey. 2002. Competence for natural transformation in *Neisseria gonorrhoeae*: components of DNA binding and uptake linked to type IV pilus expression. Mol. Microbiol. 46:749-760.

121. Srimanote, P., A. W. Paton, and J. C. Paton. 2002. Characterization of a novel type IV pilus locus encoded on the large plasmid of locus of enterocyte effacement-negative shiga-toxigenic *E. coli* strains that are virulent for humans. Infect. Immun. 70:3094-3100.

122. Kaufmann, S. H. E. 2002. Protection against tuberculosis; cytokines, T cells and macrophages. Ann. Rheum. Dis. 61:ii54-ii58.

123. Makepeace, B. L., P. J. Watt, J. E. Heckels, and M. Christodoulides. 2001. Interactions of *Neisseria gonorrhoeae* with mature human macrophages opacity proteins influence production of proinflammatory cytokines. Infect. Immun. 69:1909-1913.

124. Clemans, D. L., R. J. Bauer, J. A. Hanson, M. V. Hobbs, J. W. St. Geme III, C. F. Marrs, and J. R. Gilsdorf. 2000. Induction of proinflammatory cytokines from human respiratory epithelial cells after stimulation by nontypeable *Haemophilus influenzae*. Infect. Immun. 68:4430-4440.

125. Tarnok, A., J. Hambsch, R. Chen, and R. Varro. 2003. Cytometric bead array to measure six cytokines in twenty-five microliters of serum. Clin. Chem. 49:1000-1002.

126. Collins, F. M. 1985. Protection to mice afforded by BCG vaccines against an aerogenic challenge by three mycobacteria of decreasing virulence. Tubercle 66:257-276.

127. Delogu, G., A. Li, C. Repique, F. Collins, and S. L. Morris. 2002. DNA vaccine combinations expressing either tissue plasminogen activator signal sequence fusion proteins or ubiqitin-conjugated antigens induce sustained protective immunity in a mouse model of pulmonary tuberculosis. Infect. Immun. 70:292-302.

128. Li, Z., A. Howard, C. Kelly, G. Delogu, F. Collins, and S. L. Morris. 1999. Immunogenicity of DNA vaccines expressing tuberculosis proteins fused to tissue plasminogen activator signal sequences. Infect. Immun. 67:4780-4786.

129. Stevens, T. L., A. Bossie, V. M. Sanders, R. Fernandez-Botran, R. L. Coffman, T. R. Mosmann, and E. S. Vietta. 1988. Regulation of antibody isotype secretion by subsets of antigen-specific helper T cells. Nature 334:255-258.

130. Kachlany, S. C., P. J. Planet, R. DeSalle, D. H. Fine, and D. H. Figurski. 2001. Genes for tight adherence of *Actinobacillus actinomycetemcomitans*: from plague to pond scum. Trends Microbiol. 9:429-437.

131. Schreiner, H. C., K. Sinatra, J. B. Kaplan, D. Furgang, S. C. Kachlany, P. J. Planet, B. A. Perez, D. H. Figurski, and D. H. Fine. 2003. Tight-adherence genes of *Actinobacillus actinomycetemcomitans* are required for virulence in a rat model. PNAS. 100:7295-7300.

132. Planet, P. J., S. C. Kachlany, D. H. Fine, R. DeSalle, and D. H. Figurski. 2003. The widespread colonization island of *Actinobacillus actinomycetemcomitans*. Nature Genetics 34:193-198.

133. Freundlich, B. and N. Avdalovic. 1983. Use of gelatin/plasma coated flasks for isolating human peripheral blood monocytes. J. Immunol. Methods. 62:31-37.

134. Kobie, J. J., R. S. Wu, R. A. Kurt, S. Lou, M. K. Adelman, L. J. Whitesell, L. V. Ramanathapuram, C. L. Arteaga, and E. T. Akporriaye. 2003. Transforming growth factor beta inhibits the antigen-presenting functions and antitumor activity of dendritic cell vaccines. Cancer Res. 63:1860-1864.

135. Redpath, S., P. Gahazal, and N. R. Gascoigne. 2001. Hijacking and exploitation of IL-10 by intracellular pathogens. Trends Microbiol. 9:86-92.

136. Flesch, I. E., J. H. Hess, I. P. Oswald, and S. H. Kaufmann. 1993. Growth inhibition of *Mycobacterium bovis* by IFN-γ-stimulated macrophages: regulation by endogenous tumor necrosis factor and IL-10. Int. Immunol. 6:693-700.

137. Garbe, T. R., J. Barathi, S. Barnini, Y. Zhang, C. Abou-Zeid, D. Tang, R. Mukherjee, and D. B. Young. 1994. Transformation of mycobacterial species using hygromycin resistance as a selectable marker. Microbiology 140:133-138.

138. Reyrat, J. M., F. X. Berthet, and B. Gicquel. 1995. The urease locus of *Mycobacterium tuberculosis* and its utilization for the demonstration of allelic exchange in *Mycobacterium bovis* BCG. PNAS 92: 8768-8772.

139. Maniatis, T., E. F. Fritsch, and J. Sambrook. 1982. Molecular Cloning: A laboratory Manual. Cold Spring Harbor Laboratory Press.

140. Mdluli, K., D. R. Sherman, M. J. Hickey, B. N. Kreswirth, S. Morris, C. K. Stover, and C. E. Barry, III. 1996. Biochemical and genetic data suggests that InhA is not the primary target for activated isoniazid in *Mycobacterium tuberculosis*. J. Infect. Dis. 174:1085-1090.

141. Hatfull, G. F. Genetic transformation of mycobacteria. 1993. Trends Microbiol. 1:310-314.

142. Lee, M. H., L. Pascopella, W. R. Jacobs, Jr., and G. F. Hatfull. 1993. Site-specific integration of mycobacteriophage L5: Integration-proficient vectors for *Mycobacterium smegmatis, Mycobacterium tuberculosis* and bacille Calmette-Guerin. PNAS. 88:3111-3115.

143. Bardarov, S., J. Kriakov, C. Carriere, S. Yu, C. Vaamonde, R. A. McAdam, B. R. Bloom, G. F. Hatfull, and W. R. Jacobs, Jr. 1997. Conditional replicating mycobacteriophages: a system for tranposon delivery to *Mycobacterium tuberculosis*. PNAS. 94:10961-10966.

144. Ehrt, S., M. U. Shiloh, J. Ruan, M. Choi, S. Gunzburg, C. Nathan, Q. W. Xie, and L. W. Riley. 1997. A novel antioxidant gene from *Mycobacterium tuberculosis*. J. Exp. Med. 186:1885-1896.

145. Zhang, Y., B. Heym, B. Allen, D. B. Young, and S. T. Cole. 1992. The catalase-peroxidase gene and isoniazid resistance of *Mycobacterium tuberculosis*. Nature. 358:591-593.

146. Zhang, Y., R. Lathigra, T. Garbe, D. Catty, and D. B. Young. 1991. Genetic analysis of superoxide dismutase, the 23 kilodalton antigen of *Mycobacterium tuberculosis*. Mol. Microbiol. 5:381-391.

147. Garbe, T., D. Harris, M. Vodermeir, R. Lathigra, J. Ivanyi, and D. Young. 1993. Expression of the *Mycobacterium tuberculosis* 19-kilodalton antigen in *Mycobacterium smegmatis*: immunological analysis and evidence of glycosylation. Infect. Immun. 61:260-267.

148. Snapper, S. B., R. E. Melton, S. Mustafa, T. Kieser, and W. R. Jacobs, Jr. 1990. Isolation and characterization of efficient plasmid transformation mutants of *Mycobacterium smegmatis*. Mol. Microbiol. 4:1911-1919.

149. Belisle, J. T., L. Pascopella, J. M. Inamine, P. J. Brennan, and W. R. Jacobs, Jr. 1991. Isolation and expression of a gene cluster responsible for biosynthesis of the glycopeptidolipid antigens of *Mycobacterium avium*. J. Bacteriol. 173:6991-6997.

150. Wieles, B., T. H. M. Ottenhoff, T. M. Steenwijk, K. L. M. C. Fraken, R. R. P. DeVries, and J. A. M. Langermans. 1997. Increased intracellular survival of *Mycobacterium smegmatis* containing the *Mycobacterium leprae* thioredoxin-thioredoxin reductase gene. Infect. Immun. 65:2537-2541.

151. Rossier, O. and N. P. Cianciotto, 2001. Type II protein secretion in a subset of the PiliD-dependent processes that facilitate intracellular infection by *Legionella peumophila*. Infect. Immun. 69:2092-2098.

152. Aragon, V., S. Kurtz, A. Flieger, B. Neumeister, and N. P. Cianciotto. 2000. Secreted enzymatic activities of wild-type and pilD-deficient *Legionella pneumophila*. Infect. Immun. 68:1855-1863.

153. Hess, S., F. J. Cassels, and L. K. Pannell. 2002. Identification and characterization of hydrophobic *E. coli* virulence proteins by liquid chromatography-electrospray ionization mass spectrometry. Anal. Biochem. 302:123-130.

154. Khalil, S. B., F. J. Cassels, H. Shaheen, L. K. Pannell, N. El-Ghorab, K. Kamal, M. Mansour, S. J. Savarion, and L. F. Peruski, Jr. 1999, Characteization of an enterotoxigenic *E. coli* strain from Africa expressing a putative colonization factor. Infect. Immun. 67:4019-4026.

155. Castric, P., F. J. Cassels, and R. W. Carlson. 2001. Structural characterization of the *Pseudomonas aeruginosa* 1244 pilin glycan. J. Biol. Chem. 276:26479-26485.

156. Robey, I. F., A. B. Edmundson, S. F. Schulter, D. E. Yocum, and J. J. Marchalonis. 2002. Specificity mapping of human anti-T cell receptor monoclonal natural antibodies: defining the properties of epitope recognition promiscuity. FASEB J. 16:642-652.

157. Palumbo, J. D., M. K. Borucki, R. E. Mandrell, and L. Gorski. 2003. Serotyping of *Listeria monocytogenes* by ELISA and identification of mixed-serotype cultures by colony immunoblotting. J. Clin. Microbiol. 41:564-571.

158. Prigent-Combaret, C., G. Prensier, T. T. Le Thi, O. Vidal, P. Lejeune, and C. Dorel. 2000. Developmental pathway for biofilm formation in curli-producing *Escherichia coli* strains: role of flagella, curli and colanic acid. Environ. Microbiol. 2:450-464.

159. Pratt, L. A., and R. Kolter 1998. Genetic analysis of *Escherichia coli* biofilm formation: roles of flagella, motility, chemotaxis and type I pili. Mol. Microbiol. 30:285-293.

160. Watnick, P. I. and R. Kolter. 1999. Steps in the development of a *Vibrio cholerae* El Tor biofilm. Mol. Microbiol. 34:586-595.

161. Zhou, X., J. A. Girón, A. G. Torres, J. A. Crawford, E. Negrete, S. N. Vogel, and J. B. Kaper. 2003. Flagellin of enteropathogenic *Escherichia coli* stimulates interleukin-8 production in T84 cells. Infect. Immun. 71:2120-2129.

162. Gewirtz, A. T., P. O. Simon, C. K. Schmitt, L. J. Taylor, C. H. Hagedorn, A. D. O'Briern, A. S. Neish and J. L. Madara. 2001. *Salmonella typhimurium* translocates flagellin across intestinal epithelia, inducing a proinflammatory response. J. Clin. Invest. 107:99-109.

163. Steed, L. L., M. Setareh, and R. L. Friedman. 1991. Intracellular survival of virulent *Bordetella pertussis* in human polymorphonuclear leukocytes. J. Leuk. Biol. 50:321-330.

164. Bassoe, C. F., and C. O. Solberg. 1984. Phagocytosis of *Staphylococcus aureus* by human leukocytes: quantitation by a flow cytometric and microbiological method. Acta. Pathol. Microbiol. Immunol. Scand. Sect. C. 92:43-50.

165. Hed, J. Methods for distinguishing ingested from adhering particles. 1986. Methods Enzymol. 6:198-204.

166. Ohman, L., J, Hed, and O, Stendahl. 1975. Interaction between human polymorphonuclear leukocytes and two different strains of type I fimbriae-bearing *E. coli*. J. Infect. Dis. 146:751-757.

167. Day, R. B., Y. Wang, K. K. Knox, R. Pasula, W. J. Martin, and H. L. Twigg. 2003. Alveolar macrophages from HIV infected subjects are resistant to *Mycobacterium tuberculosis* in vitro. Am. J. Respir. Cell. Mol. Biol. Sep. 11, 2003. In Press.
168. Gilot, P., P. André, and J. Content. 1999 *Listeria monocytogenes* possesses adhesins for fibronectin. Infect Immun 67: 6698-6701.
169. Kuusela, P., T. Vartio, M. Vuento, and E. B. Myhre. 1985. Attachment of staphylococci and streptococci on fibronectin, fibronectin fragments, and fibrinogen bound on a solid phase. Infect Immun 50: 77-81.
170. Mckeown-Longo, P. J. (1987) Fibronectin-cell surface interactions. Rev Infect Dis 9: S322-S334.
171. Patti, J., M., B. L. Allen, M. J. McGavin, and M. Hook. 1994. MSCRAMM-mediated adherence of microorganisms to host tissues. Ann. Rev. Microbiol. 48:585-617.
172. Marques, M. A., V. L. Antonio, E. N. Sarno, P. J. Brennan, and M. C. Pessolani. 2001. Binding of α2-laminin by pathogenic and non-pathogenic mycobacteria and adherence to Schwann cells. Microbial. Pathogenesis 50:23-28.
173. Fink, D. L., B. A. Green, and J. W. St. Geme III. 2002. The *Haemophilus influenzae* Hap autransporter binds to fibronectin, laminin, and collagen IV. Infect. Immun. 70:4902-4907.
174. Zogaj, X., M. Nimtz, M. Rohde, W. Bokranz, and U. Romling. 2001. The multicellular morphotypes of *Salmonella typhimurium* and *Escherichia coli* produce cellulose as the second component of the extracellular matrix. Mol. Microbiol. 39:1452-1463.
175. Friedman, R. L., K. Nordensson, L. Wilson, E. T. Akporiaye, and D. E. Yocum. 1992. Uptake and intracellular survival of *Bordetella pertussis* in human macrophages. Infect. Immun. 60:4578-4585.
176. Hess, S., F. Cassels, J. Cisar, L. K. Pannell. 2003. Characterization of hydrophobic fimbrial membrane proteins by LC-MS and LC-MS/MS, Abstracts 51st Amer. Soc. Mass Spectrom. Montreal, #10:55.
177. Hess, S., F. Cassels, L. K. Pannell. 2002. Identification and characterization of hydrophobic *Escherichia coli* virulence proteins by liquid chromatography-electrospray ionization mass spectrometry, Anal. Biochem., 302, 123-130.
178. Ryu, H., Y. S. Kim, P. Grange, F. J. Cassels, 2001. *Escherichia coli* strain RDEC-I AF/R1 endogenous fimbrial glycoconjugate receptor molecules in rabbit small intestine. Infect. Immun. 69, 640-649

Obviously, numerous modifications and variations of the present invention are possible in light of the above teachings. It is therefore to be understood that within the scope of the appended claims, the invention may be practiced otherwise than as specifically described herein.

The invention claimed is:

1. Isolated and purified pili obtained from *Mycobacterium tuberculosis*, wherein the pili:

(a) are macromolecules which comprise pilin monomers, wherein the pilin monomers comprise proteins having a molecular weight of 14-25 kDa, (b) are in the form of aggregated fibers, wherein the fibers have a width of 2 to 7 nm and a length of at least 5 microns, (c) are immunogenic, and (d) the aggregated fibers form a highly hydrophobic network.

2. The pili of claim 1, which have been separated from said *Mycobacterium tuberculosis* by mechanical shearing, differential centrifugation or isopycnic separation.

3. The pili of claim 1, wherein the fibers have a length of at least 10 microns.

4. The pili of claim 1, wherein the pilin monomers comprise SEQ ID NO: 1.

5. The pili of claim 1, wherein the pilin monomers comprise SEQ ID NO: 2.

6. The pili of claim 1, wherein the pilin monomers comprise SEQ ID NO: 3.

7. The pili of claim 1, wherein the pilin monomers comprise SEQ ID NO: 5.

8. A method of producing the pili of claim 1, comprising subjecting cells of *Mycobacterium tuberculosis* which produce the pili to mechanical shearing, differential centrifugation or isopycnic separation and then isolating the pili from the cells.

9. A method of detecting a *Mycobacterium tuberculosis* infection in a subject, comprising contacting a body fluid from the subject with the pili of claim 1 and assaying for the presence of an antibody to the pili.

10. The method of claim 9, wherein the subject is a human.

11. The method of claim 9, wherein the body fluid is serum.

12. A method of inducing an immune response against *Mycobacterium tuberculosis*, comprising administering an effective amount of the pili of claim 1 to a subject in need thereof.

13. The method of claim 9, wherein the subject is a human.

* * * * *

SEQUENCE LISTING

```
<160> NUMBER OF SEQ ID NOS: 5

<210> SEQ ID NO 1
<211> LENGTH: 14
<212> TYPE: PRT
<213> ORGANISM: Mycobacterium tuberculosis

<400> SEQUENCE: 1

Pro Gly Ala Ala Pro Pro Pro Pro Ala Ala Gly Gly Gly Ala
 1               5                  10

<210> SEQ ID NO 2
<211> LENGTH: 114
<212> TYPE: PRT
<213> ORGANISM: Mycobacterium tuberculosis

<400> SEQUENCE: 2

Met Leu Ala Arg Ser Leu Ser Tyr Arg His Arg Met Tyr Arg Phe Ala
 1               5                  10                  15

Cys Arg Thr Leu Met Leu Ala Ala Cys Ile Leu Ala Thr Gly Val Ala
                20                  25                  30

Gly Leu Gly Val Gly Ala Gln Ser Ala Ala Gln Thr Ala Pro Val Pro
            35                  40                  45

Asp Tyr Tyr Trp Cys Pro Gly Gln Pro Phe Asp Pro Ala Trp Gly Pro
        50                  55                  60

Asn Trp Asp Pro Tyr Thr Cys His Asp Asp Phe His Arg Asp Ser Asp
    65                  70                  75                  80

Gly Pro Asp His Ser Arg Asp Tyr Pro Gly Pro Ile Leu Glu Gly Pro
                85                  90                  95

Val Leu Asp Asp Pro Gly Ala Ala Pro Pro Pro Ala Ala Gly Gly
                100                 105                 110

Gly Ala
```

```
<210> SEQ ID NO 3
<211> LENGTH: 20
<212> TYPE: PRT
<213> ORGANISM: Mycobacterium tuberculosis

<400> SEQUENCE: 3

Cys His Asp Asp Phe His Arg Asp Ser Asp Gly Pro Asp His Ser Arg
  1               5                  10                  15

Asp Tyr Pro Gly
             20

<210> SEQ ID NO 4
<211> LENGTH: 312
<212> TYPE: DNA
<213> ORGANISM: Mycobacterium tuberculosis

<400> SEQUENCE: 4
atgtaccggt tcgcgtgccg cacgctcatg ctggcggcgt gcatcctggc cacgggtgtg       60
gcgggtctcg gggtcggcgc gcagtccgca gcccaaaccg cgccggtgcc cgactactac      120
tggtgcccgg ggcagccttt cgaccccgca tggggcccca actgggatcc ctacacctgc      180
catgacgact tccaccgcga cagcgacggc cccgaccaca gccgcgacta ccccggaccc      240
atcctcgaag gtcccgtgct tgacgatccc ggtgctgcgc cgccgccccc ggctgccggt      300
ggcggcgcat ag                                                         312

<210> SEQ ID NO 5
<211> LENGTH: 103
<212> TYPE: PRT
<213> ORGANISM: Mycobacterium tuberculosis

<400> SEQUENCE: 5

Met Tyr Arg Phe Ala Cys Arg Thr Leu Met Leu Ala Ala Cys Ile Leu
  1               5                  10                  15

Ala Thr Gly Val Ala Gly Leu Gly Val Gly Ala Gln Ser Ala Ala Gln
             20                  25                  30

Thr Ala Pro Val Pro Asp Tyr Tyr Trp Cys Pro Gly Gln Pro Phe Asp
         35                  40                  45

Pro Ala Trp Gly Pro Asn Trp Asp Pro Tyr Thr Cys His Asp Asp Phe
 50                  55                  60

His Arg Asp Ser Asp Gly Pro Asp His Ser Arg Asp Tyr Pro Gly Pro
 65                  70                  75                  80

Ile Leu Glu Gly Pro Val Leu Asp Asp Pro Gly Ala Ala Pro Pro Pro
                 85                  90                  95

Pro Ala Ala Gly Gly Gly Ala
            100
```